United States Patent
Cunningham et al.

(10) Patent No.: US 9,193,705 B2
(45) Date of Patent: Nov. 24, 2015

(54) SMALL MOLECULE INHIBITORS OF EBOLA AND LASSA FEVER VIRUSES AND METHODS OF USE

(75) Inventors: James Cunningham, Wellesley, MA (US); Kyungae Lee, Newton, MA (US); Tao Ren, West Roxbury, MA (US); Kartik Chandran, Brooklyn, NY (US)

(73) Assignees: President and Fellows of Harvard College, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 13 days.

(21) Appl. No.: 13/818,790

(22) PCT Filed: Sep. 1, 2011

(86) PCT No.: PCT/US2011/050164
§ 371 (c)(1),
(2), (4) Date: May 6, 2013

(87) PCT Pub. No.: WO2012/031090
PCT Pub. Date: Mar. 8, 2012

(65) Prior Publication Data
US 2013/0231332 A1 Sep. 5, 2013

Related U.S. Application Data

(60) Provisional application No. 61/379,138, filed on Sep. 1, 2010.

(51) Int. Cl.
| | | |
|---|---|---|
| *C07D 401/04* | (2006.01) |
| *C07D 211/58* | (2006.01) |
| *C07D 207/14* | (2006.01) |
| *C07D 243/08* | (2006.01) |
| *C07D 405/04* | (2006.01) |
| *C07D 417/04* | (2006.01) |
| *C07C 311/29* | (2006.01) |
| *C07D 207/08* | (2006.01) |

(52) U.S. Cl.
CPC .......... *C07D 401/04* (2013.01); *C07C 311/29* (2013.01); *C07D 207/08* (2013.01); *C07D 207/14* (2013.01); *C07D 211/58* (2013.01); *C07D 243/08* (2013.01); *C07D 405/04* (2013.01); *C07D 417/04* (2013.01)

(58) Field of Classification Search
CPC ........................... C07D 401/04; C07D 211/58
USPC .......................................... 514/218; 546/208
See application file for complete search history.

(56) References Cited

U.S. PATENT DOCUMENTS

2006/0160851 A1* 7/2006 Ebdrup et al. ................. 514/316
2009/0053263 A1  2/2009 Cunningham et al.

OTHER PUBLICATIONS

CAS Registry No. 1015667-60-3 as entered Apr. 18, 2008.*
International Search Report dated Apr. 30, 2012, from PCT/US2011/050164.
Wolf et al., "A broad-spectrum antiviral targeting entry of enveloped viruses," PNAS, 107(7):3157-3162 (2010).

* cited by examiner

*Primary Examiner* — John Mabry
(74) *Attorney, Agent, or Firm* — Foley Hoag LLP

(57) ABSTRACT

The present invention relates to compositions and methods for the treatment of infection by enveloped viruses, such as Ebola and Lassa fever viruses.

14 Claims, 3 Drawing Sheets

FIG. 1

Figure 2:
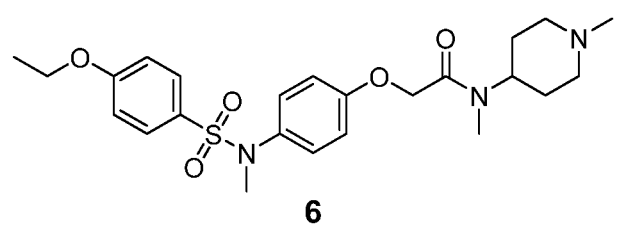
Figure 2:
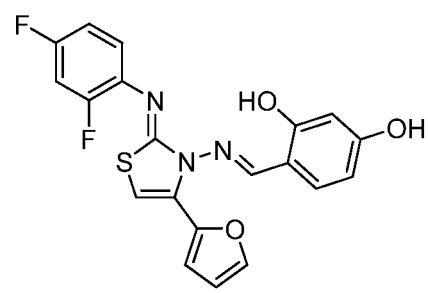
Figure 2:
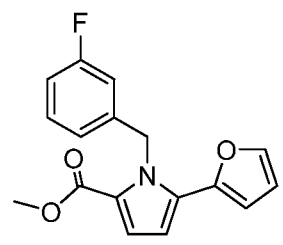
Figure 3:
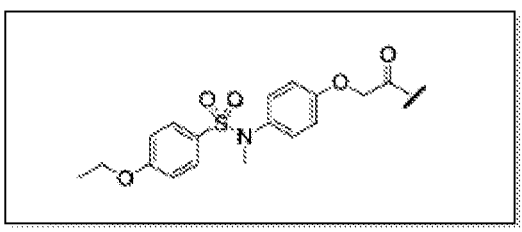
Figure 3:
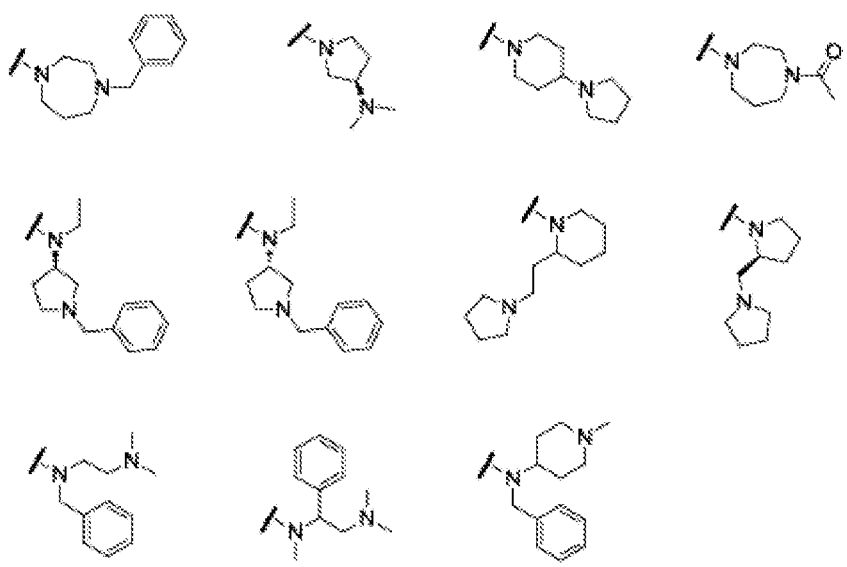

Native GP → GP cleaved → Infection

GP1: MUC, 18K (-COOH, -NH₂)
GP2 cathepsin protease inhibitors compounds of the invention

6

7

8

SMALL MOLECULE INHIBITORS OF EBOLA AND LASSA FEVER VIRUSES AND METHODS OF USE

RELATED APPLICATIONS

This application is the National Stage application of PCT/US11/050164, filed Sep. 1, 2011, which claims the benefit of priority to U.S. Provisional Patent Application Ser. No. 61/379,138, filed Sep. 1, 2010, the contents of which are hereby incorporated by reference.

GOVERNMENT SUPPORT

This invention was made with government support under AI057159 awarded by the National Institutes of Health. The government has certain rights in the invention.

BACKGROUND

Ebolaviruses (EboV) are enveloped negative-sense RNA viruses that cause sporadic outbreaks of rapidly fatal zoonotic infection. EboV is transmitted by close contact and virus levels increase by 75-fold/day for several days after initial infection. The clinical symptoms are manifestations of the massive production of pro-inflammatory cytokines, including interferon-α and TNF-α in response to infection. The endothelial cell dysfunction associated with "cytokine storm" results in capillary leak, hypovolemic shock, disseminated intravascular coagulation and inadequate perfusion of major organs. In many outbreaks, the mortality rate from EboV infection exceeds 75% in 14 days. Current therapy is supportive; there is no effective anti-EboV vaccine or therapy. The unpredictable onset, ease of transmission, rapidity of progression, high mortality, and bio-terrorism potential have created a high level of public concern about EboV. Therefore, development of anti-EboV drugs is a high priority.

Recent studies have identified promising drug targets. Previously, it was found that stepwise proteolytic cleavage of EboV envelope glycoprotein GP by the lysosomal cysteine proteases cathepsin L (Cat L) and cathepsin B (Cat B) is required for infection; and therefore, inhibitors of Cat L and Cat B are potential anti-EboV drugs (see, for example, US Patent Application publication number 2009/0053263 to Cunningham, J. et al.).

SUMMARY

One aspect of the invention relates to a compound represented by formula I:

$$R^1-A^1-R^2 \quad \text{I}$$

or a pharmaceutically acceptable salt, solvate, hydrate, prodrug, chemically-protected form, enantiomer or stereoisomer thereof; wherein, independently for each occurrence, $A^1$ is $$A$$

is a six-membered aryl diradical or a six-membered heteroaryl diradical;

$R^1$ is [structures shown]

$R^2$ is [structures shown]

$A^2$ is a substituted or unsubstituted six-membered aryl or heteroaryl ring;

$A^3$ is a substituted or unsubstituted five- or six-membered cycloalkyl or heterocycloalkyl ring;

$A^4$ is a substituted or unsubstituted five-, six-, or seven-membered heterocycloalkyl ring;

$A^5$ is a substituted or unsubstituted aralkyl moiety;

X is a bond,

[structures shown]

$R^3$ is hydrogen, halo, alkyl or haloalkyl;

$R^4$ is hydrogen, alkyl, haloalkyl, aryl, heteroaryl, aralkyl, heteroaralkyl, alkylcarbonyl, heteroalkyl, haloalkyl, arylcarbonyl, heteroarylcarbonyl, aralkylcarbonyl or heteroaralkylcarbonyl; and $R^5$ is hydrogen, alkyl, haloalkyl or alkyl substituted with one or two substituents independently selected from the group consisting of halo, cyano, haloalkyl, carbocyclyl, heterocyclyl, aryl, heteroaryl, carbocyclylalkyl, heterocyclylalkyl, aralkyl, heteroaralkyl, hydroxy, alkyloxy, haloalkyloxy, carbocyclyloxy, heterocyclyloxy, aryloxy, heteroaryloxy, carbocyclylalkyloxy, heterocyclylalkyloxy, aralkyloxy, heteroaralkyloxy, alkylcarbonyloxy, halo alkylcarbonyloxy, carbocyclylcarbonyloxy, heterocyclylcarbonyloxy, arylcarbonyloxy, heteroarylcarbonyloxy, carbocyclylalkylcarbonyloxy, heterocyclylalkylcarbonyloxy, aralkylcarbonyloxy, heteroaralkylcarbonyloxy, carboxy, alkyloxycarbonyl, halo alkyloxycarbonyl, carbocyclyloxycarbonyl, heterocyclyloxycarbonyl, aryloxycarbonyl, heteroaryloxycarbonyl, carbocyclylalkyloxycarbonyl, heterocyclylalkyloxycarbonyl, aralkyloxycarbonyl, heteroaralkylcarbonyloxy, amino and amido; or $R^5$ when bonded to a carbon substituted with an $R^4$ may optionally be, taken together with the $R^4$, an oxo;

provided that the compound is not

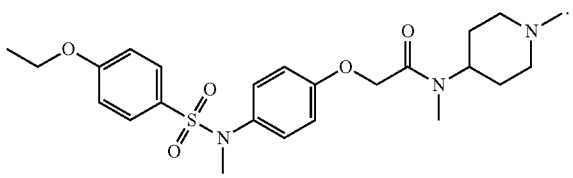 [SMILES: CCOc1ccc(S(=O)(=O)N(C)c2ccc(OCC(=O)N(C)C3CCN(C)CC3)cc2)cc1]

Another aspect of the invention relates to a compound represented by formula III:

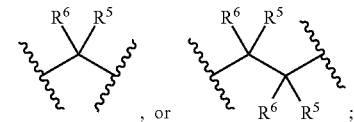

or a pharmaceutically acceptable salt, solvate, hydrate, prodrug, chemically-protected form, enantiomer or stereoisomer thereof; wherein, independently for each occurrence,

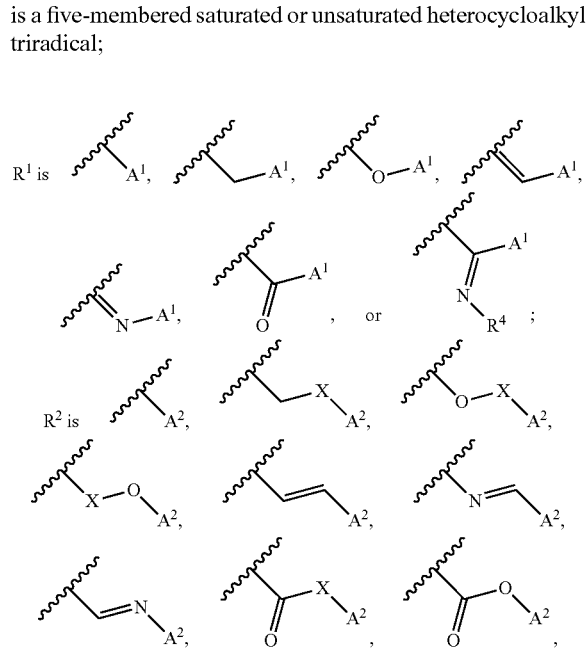

is a five-membered saturated or unsaturated heterocycloalkyl triradical;

$A^1$ is a substituted or unsubstituted six-membered aryl or heteroaryl ring;

$A^2$ is a substituted or unsubstituted six-membered aryl or heteroaryl ring;

$A^3$ is a substituted or unsubstituted five-membered aryl or heteroaryl ring;

X is a bond, $R^4$ is hydrogen, alkyl, haloalkyl, aryl, heteroaryl, aralkyl, heteroaralkyl, alkylcarbonyl, haloalkyl, arylcarbonyl, heteroarylcarbonyl, aralkylcarbonyl or heteroaralkylcarbonyl;

$R^5$ is hydrogen, alkyl, haloalkyl or alkyl substituted with one or two substituents independently selected from the group consisting of halo, cyano, haloalkyl, carbocyclyl, heterocyclyl, aryl, heteroaryl, carbocyclylalkyl, heterocyclylalkyl, aralkyl, heteroaralkyl, hydroxy, alkyloxy, haloalkyloxy, carbocyclyloxy, heterocyclyloxy, aryloxy, heteroaryloxy, carbocyclylalkyloxy, heterocyclylalkyloxy, aralkyloxy, heteroaralkyloxy, alkylcarbonyloxy, halo alkylcarbonyloxy, carbocyclylcarbonyloxy, heterocyclylcarbonyloxy, arylcarbonyloxy, heteroarylcarbonyloxy, carbocyclylalkylcarbonyloxy, heterocyclylalkylcarbonyloxy, aralkylcarbonyloxy, heteroaralkylcarbonyloxy, carboxy, alkyloxycarbonyl, halo alkyloxycarbonyl, carbocyclyloxycarbonyl, heterocyclyloxycarbonyl, aryloxycarbonyl, heteroaryloxycarbonyl, carbocyclylalkyloxycarbonyl, heterocyclylalkyloxycarbonyl, aralkyloxycarbonyl, heteroaralkylcarbonyloxy, amino and amido; or $R^5$ when bonded to a carbon substituted with an $R^4$ may optionally be, taken together with the $R^4$, an oxo; and $R^6$ is hydrogen, halo, alkyl or haloalkyl;

provided the compound is not

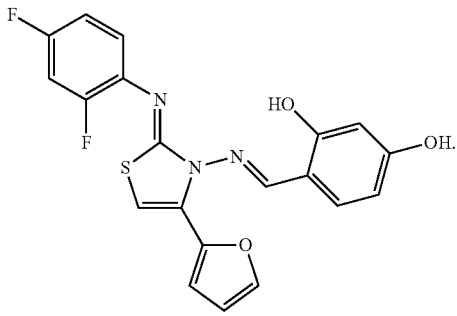 [SMILES: Oc1ccc(/C=N/n2c(-c3ccco3)cs/c2=N\c2ccc(F)cc2F)c(O)c1]

Another aspect of the invention relates to a compound represented by formula V:
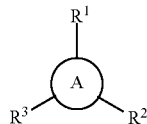

V or a pharmaceutically acceptable salt, solvate, hydrate, prodrug, chemically-protected form, enantiomer or stereoisomer thereof; wherein, independently for each occurrence,
is a five-membered heteroaryl triradical;
$R^1$ is
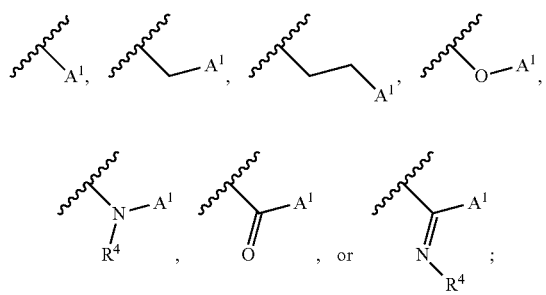

, or ;

$R^2$ is
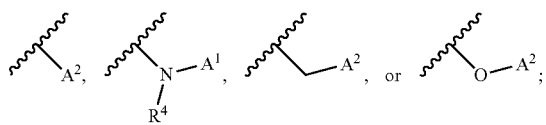

, or ;

$R^3$ is halo, cyano, haloalkyl, hydroxy, alkyloxy, haloalkyloxy, alkylcarbonyloxy, haloalkylcarbonyloxy, carboxy, alkyloxycarbonyl, haloalkyloxycarbonyl, amino, nitro, or amido;

$A^1$ is a substituted or unsubstituted six-membered aryl or heteroaryl ring;

$A^2$ is a substituted or unsubstituted five-membered heteroaryl ring; and $R^4$ is hydrogen, alkyl, haloalkyl, aryl, heteroaryl, aralkyl, heteroaralkyl, alkylcarbonyl, haloalkyl, arylcarbonyl, heteroarylcarbonyl, aralkylcarbonyl or heteroaralkylcarbonyl; provided the compound is not

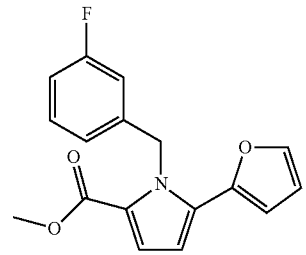

.

Another aspect of the invention relates to the use of compounds of formula I, III, or V, or a pharmaceutically acceptable salt, solvate, hydrate, prodrug, chemically-protected form, enantiomer or stereoisomer thereof, for treating viral infection, comprising administering to a subject in need thereof an effective amount of a compound of formula I, III, or V, or a pharmaceutically acceptable salt, solvate, hydrate, prodrug, chemically-protected form, enantiomer or stereoisomer thereof. In certain embodiments, the viral infection is an Ebola or Lassa fever infection.

Additional aspects, embodiments, and advantages of the invention are discussed below in detail.

BRIEF DESCRIPTION OF THE FIGURES

FIG. 1 depicts a possible model of infection by EboV GP: cathepsin proteolysis removes part of EboV GP1; and cleaved GP is further activated to mediate virus fusion to cells. Although applicant is not bound by a mechanism, it is believed that some of the compounds of the invention may at least partially inhibit the activation of the cleaved GP.

FIG. 2 depicts selected compounds 6, 7, and 8.

FIG. 3 depicts selected analogs of compound 6; the compounds depicted inhibit >90% of Ebola at 10 μM.

DETAILED DESCRIPTION

Overview

As noted above, it has been found that stepwise proteolytic cleavage of EboV envelope glycoprotein GP by the lysosomal cysteine proteases cathepsin L (Cat L) and cathepsin B (Cat B) is required for Ebola infection. However, because cathepsin cleavage of EboV GP is necessary, but not sufficient for infection, it was hypothesized that the molecular basis of the additional steps might yield targets for viral inhibition. To this end, a small molecule library was screened for compounds that specifically blocked infection by vesicular stomatitis virus (VSV) particles engineered to express the EboV GP and to encode luciferase marker. As a control, VSV luc particles bearing the native VSV G glycoprotein were also tested. After screening the library, several potent ($IC_{50}$ less than about 10 mM) and EboV specific compounds were found. Three such compounds, compounds 6, 7, and 8, are shown in FIG. 1.

Studies of previous compounds established that the target(s) for the inhibitors are in the cell and not in the virus. In addition, it was further shown that the compounds are not cathepsin inhibitors. Although Applicant is not bound by a mechanism, it is possible that the compounds inhibit trafficking of the virus particles to late endosomes or lysosomes. Late endosomes/lysosomes are the site where Ebola GP mediates fusion of the virus to the cell membrane, thus forming a pore that is the conduit for transfer of the Ebola virus genome into the cell cytoplasm. Alternatively, again not intending to be bound by a mechanism, the compounds of the invention may block EboV GP binding to a receptor.

In certain embodiments, chemical dissection of the anti-EboV activity of various inhibitors may be performed, resulting in the preparation and testing of derivative compounds. In certain embodiments, a derivative compound may be a weak EboV inhibitor, but a highly active LSV infection inhibitor. Previous studies have also suggested that EboV and LSV infection may be mediated by distinct but closely related pathways that are inhibited by these compounds.

DEFINITIONS

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "lower" when appended to any of the groups listed below indicates that the group contains less than seven carbons (i.e. six carbons or less). For example "lower alkyl" refers to an alkyl group containing 1-6 carbons, and "lower alkenyl" refers to an alkenyl group containing 2-6 carbons.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon.

For purposes of this invention, the chemical elements are identified in accordance with the Periodic Table of the Elements, CAS version, Handbook of Chemistry and Physics, 67th Ed., 1986-87, inside cover.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means an aliphatic or cyclic hydrocarbon radical containing from 1 to 12 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, and 1-cyclohexylethyl.

The term "alkylene" is art-recognized, and as used herein pertains to a bidentate moiety obtained by removing a hydrogen atom from an alkyl group, as defined above.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "carbocyclyl" as used herein means monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g. phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "heterocyclyl", as used herein refers to a radical of a non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system, and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, halo alkoxysulfonyloxy, fluoroalkoxysulfonyloxy, alkenyloxysulfonyloxy, alkynyloxysulfonyloxy, alkylsulfinyloxy, halo alkylsulfinyloxy, fluoroalkylsulfinyloxy, alkenylsulfinyloxy, alkynylsulfinyloxy, alkoxysulfinyloxy, halo alkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, cyclic acetal, and any of said substituents bound to the heterocyclyl group through an alkylene moiety (e.g. methylene).

The term "cyclic acetal" refers to a bidentate moiety represented by —O-alkylene-O—. Representative examples of cyclic acetals include, but are not limited to, methylenedioxy, ethylenedioxy, propylenedioxy, butylenedioxy;

The term "arylene," is art-recognized, and as used herein pertains to a bidentate moiety obtained by removing a hydrogen atom from an aryl ring, as defined above.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-ylethyl.

The term "aryl," as used herein means a phenyl group, naphthyl or anthracenyl group. The aryl groups of the present invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, halo alkoxysulfonyloxy, fluoroalkoxysulfonyloxy, alkenyloxysulfonyloxy, alkynyloxysulfonyloxy, alkylsulfinyloxy, halo alkylsulfinyloxy, fluoroalkylsulfinyloxy, alkenylsulfinyloxy, alkynylsulfinyloxy, alkoxysulfinyloxy, halo alkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, cyclic acetal, and any of said substituents bound to the heterocyclyl group through an alkylene moiety (e.g. methylene).

The term "heteroaryl" as used herein refers to a radical of an aromatic ring, including, but not limited to, monocyclic, bicyclic and tricyclic rings, which has 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, halo alkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, halo alkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, halo alkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heteroaryl group through an alkylene moiety (e.g. methylene).

The term "heteroarylene," is art-recognized, and as used herein pertains to a bidentate moiety obtained by removing a hydrogen atom from a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein all the hydrogens are replaced with fluorines.

The term "hydroxy" as used herein means an —OH group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkenyloxy", "alkynyloxy", "carbocyclyloxy", and "heterocyclyloxy" are likewise defined.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy. The term "fluoroalkyloxy" is likewise defined.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen. The terms "heteroaryloxy" is likewise defined.

The term "arylalkoxy" or "arylalkyloxy" as used herein means an arylalkyl group, as defined herein, appended to the parent molecular moiety through an oxygen. The term "heteroarylalkoxy" is likewise defined. Representative examples of aryloxy and heteroarylalkoxy include, but are not limited to, 2-chlorophenylmethoxy, 3-trifluoromethyl-phenylethoxy, and 2,3-dimethylpyridinylmethoxy.

The term "sulfhydryl" or "thio" as used herein means a —SH group.

The term "alkylthio" as used herein means an alkyl group, as defined herein, appended to the parent molecular moiety through a sulfur. Representative examples of alkylthio include, but are not limited, methylthio, ethylthio, tert-butylthio, and hexylthio. The terms "haloalkylthio", "fluoroalkylthio", "alkenylthio", "alkynylthio", "carbocyclylthio", and "heterocyclylthio" are likewise defined.

The term "arylthio" as used herein means an aryl group, as defined herein, appended to the parent molecular moiety through an sulfur. The term "heteroarylthio" is likewise defined.

The term "arylalkylthio" or "aralkylthio" as used herein means an arylalkyl group, as defined herein, appended to the parent molecular moiety through an sulfur. The term "heteroarylalkylthio" is likewise defined.

The term "sulfonyl" as used herein refers to —S(=O)$_2$— group.

The term "sulfonic acid" as used herein refers to —S(=O)$_2$OH.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl. The terms "haloalkylsulfonyl", "fluoroalkylsulfonyl", "alkenylsulfonyl", "alkynylsulfonyl", "carbocyclylsulfonyl", "heterocyclylsulfonyl", "arylsulfonyl", "aralkylsulfonyl", "heteroarylsulfonyl" and "heteroaralkylsulfonyl" are likewise defined.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl. The terms "haloalkoxysulfonyl", "fluoroalkoxysulfonyl", "alkenyloxysulfonyl", "alkynyloxysulfonyl", "carbocyclyloxysulfonyl", "heterocyclyloxysulfonyl", "aryloxysulfonyl", "aralkyloxysulfonyl", "heteroaryloxysulfonyl" and "heteroaralkyloxysulfonyl" are likewise defined.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "aminosulfonyl" as used herein means an amino group, as defined herein, appended to the parent molecular moiety through a sulfonyl group.

The term "sulfinyl" as used herein refers to —S(=O)— group. Sulfinyl groups are as defined above for sulfonyl groups. The term "sulfinic acid" as used herein refers to —S(=O)OH.

The term "oxy" refers to a —O— group.

The term "carbonyl" as used herein means a —C(=O)— group.

The term "thiocarbonyl" as used herein means a —C(=S)— group.

The term "formyl" as used herein means a —C(=O)H group.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl. The terms "haloalkylcarbonyl", "fluoroalkylcarbonyl", "alkenylcarbonyl", "alkynylcarbonyl", "carbocyclylcarbonyl", "heterocyclylcarbonyl", "arylcarbonyl", "aralkylcarbonyl", "heteroarylcarbonyl", and "heteroaralkylcarbonyl" are likewise defined.

The term "carboxy" as used herein means a —CO₂H group.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl. The terms "haloalkoxycarbonyl", "fluoroalkoxycarbonyl", "alkenyloxycarbonyl", "alkynyloxycarbonyl", "carbocyclyloxycarbonyl", "heterocyclyloxycarbonyl", "aryloxycarbonyl", "aralkyloxycarbonyl", "heteroaryloxycarbonyl", and "heteroaralkyloxycarbonyl" are likewise defined.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. The terms "halo alkylcarbonyloxy", "fluoroalkylcarbonyloxy", "alkenylcarbonyloxy", "alkynylcarbonyloxy", "carbocyclylcarbonyloxy", "heterocyclylcarbonyloxy", "arylcarbonyloxy", "aralkylcarbonyloxy", "heteroarylcarbonyloxy", and "heteroaralkylcarbonyloxy" are likewise defined.

The term "alkylsulfonyloxy" as used herein means an alkylsulfonyl group, as defined herein, appended to the parent molecular moiety through an oxygen atom. The terms "haloalkylsulfonyloxy", "fluoroalkylsulfonyloxy", "alkenylsulfonyloxy", "alkynylsulfonyloxy", "carbocyclylsulfonyloxy", "heterocyclylsulfonyloxy", "arylsulfonyloxy", "aralkylsulfonyloxy", "heteroarylsulfonyloxy", "heteroaralkylsulfonyloxy", "haloalkoxysulfonyloxy", "fluoroalkoxysulfonyloxy", "alkenyloxysulfonyloxy", "alkynyloxysulfonyloxy", "carbocyclyloxysulfonyloxy", "heterocyclyloxysulfonyloxy", "aryloxysulfonyloxy", "aralkyloxysulfonyloxy", "heteroaryloxysulfonyloxy" and "heteroaralkyloxysulfonyloxy"

The term "amino" as used herein refers to —NH₂ and substituted derivatives thereof wherein one or both of the hydrogens are independently replaced with substituents selected from the group consisting of alkyl, haloalkyl, fluoroalkyl, alkenyl, alkynyl, carbocyclyl, heterocycyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarnbonyl, heteroaralkylcarbonyl and the sufonyl and sulfinyl groups defined above; or when both hydrogens together are replaced with an alkylene group (to form a ring which contains the nitrogen). Representative examples include, but are not limited to methylamino, acetylamino, and dimethylamino.

The term "amido" as used herein means an amino group, as defined herein, appended to the parent molecular moiety through a carbonyl.

The term "cyano" as used herein means a —C≡N group.

The term "nitro" as used herein means a —NO₂ group.

The term "azido" as used herein means a —N₃ group.

The term "phosphinyl" as used herein includes —PH₃ and substituted derivatives thereof wherein one, two or three of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "phosphoryl" as used herein refers to —P(=O)OH₂ and substituted derivatives thereof wherein one or both of the hydroxyls are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "silyl" as used herein includes H₃Si— and substituted derivatives thereof wherein one, two or three of the hydrogens are independently replaced with substituents selected from alkyl, haloalkyl, fluoroalkyl, alkenyl, alkynyl, carbocyclyl, heterocyclyl, aryl, aralkyl, heteroaryl, and heteroaralkyl. Representative examples include trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The abbreviations Me, Et, Ph, Bn, Tf, Nf, Ts, and Ms represent methyl, ethyl, phenyl, benzyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

The term "viral infection" as used herein refers to infection by a viral pathogen wherein there is clinical evidence of the infection based on symptoms or based on the demonstration of the presence of the viral pathogen in a biological sample from the individual. As used herein an "individual" refers to an animal, preferably a mammal, including both non-human mammals and humans, and more preferably, refers to a human.

The expression "effective amount" when used to describe therapy to an individual suffering from a viral infection refers to the amount of a compound that results in a therapeutically useful effect on the symptoms of the viral infection and/or a reduction in viral load.

"Treatment of a viral infection" as used herein encompasses alleviating, reducing the frequency of, or eliminating one or more symptoms of the infection and/or a reducing the viral load.

Exemplary Compounds

One aspect of the invention relates to a compound represented by formula I:

I or a pharmaceutically acceptable salt, solvate, hydrate, prodrug, chemically-protected form, enantiomer or stereoisomer thereof; wherein, independently for each occurrence,

is a six-membered aryl diradical or a six-membered heteroaryl diradical;

$R^1$ is

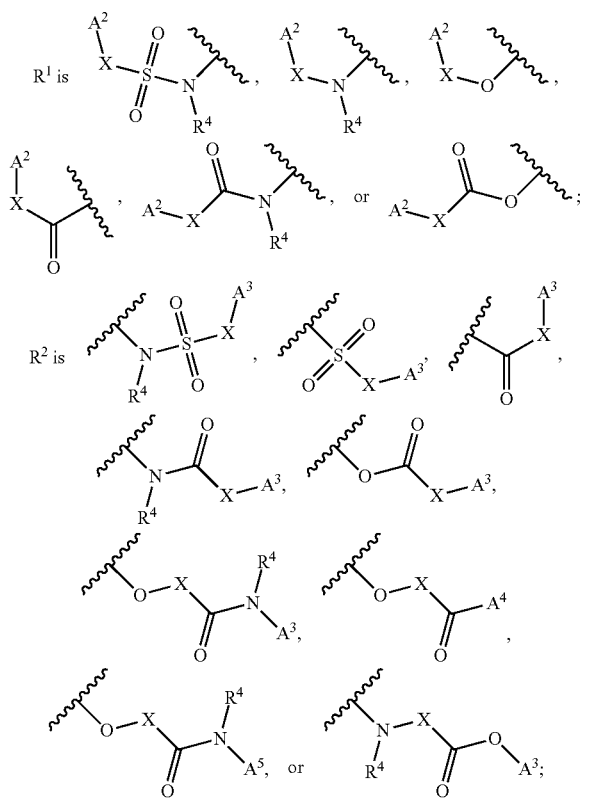

$A^2$ is a substituted or unsubstituted six-membered aryl or heteroaryl ring;

$A^3$ is a substituted or unsubstituted five- or six-membered cycloalkyl or heterocycloalkyl ring;

$A^4$ is a substituted or unsubstituted five-, six-, or seven-membered heterocycloalkyl ring;

$A^5$ is a substituted or unsubstituted aralkyl moiety;

X is a bond,

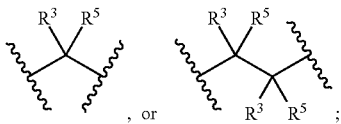

$R^3$ is hydrogen, halo, alkyl or haloalkyl;

$R^4$ is hydrogen, alkyl, haloalkyl, aryl, heteroaryl, aralkyl, heteroaralkyl, alkylcarbonyl, heteroalkyl, haloalkyl, arylcarbonyl, heteroarylcarbonyl, aralkylcarbonyl or heteroaralkylcarbonyl; and $R^5$ is hydrogen, alkyl, haloalkyl or alkyl substituted with one or two substituents independently selected from the group consisting of halo, cyano, haloalkyl, carbocyclyl, heterocyclyl, aryl, heteroaryl, carbocyclylalkyl, heterocyclylalkyl, aralkyl, heteroaralkyl, hydroxy, alkyloxy, haloalkyloxy, carbocyclyloxy, heterocyclyloxy, aryloxy, heteroaryloxy, carbocyclylalkyloxy, heterocyclylalkyloxy, aralkyloxy, heteroaralkyloxy, alkylcarbonyloxy, halo alkylcarbonyloxy, carbocyclylcarbonyloxy, heterocyclylcarbonyloxy, arylcarbonyloxy, heteroarylcarbonyloxy, carbocyclylalkylcarbonyloxy, heterocyclylalkylcarbonyloxy, aralkylcarbonyloxy, heteroaralkylcarbonyloxy, carboxy, alkyloxycarbonyl, halo alkyloxycarbonyl, carbocyclyloxycarbonyl, heterocyclyloxycarbonyl, aryloxycarbonyl, heteroaryloxycarbonyl, carbocyclylalkyloxycarbonyl, heterocyclylalkyloxycarbonyl, aralkyloxycarbonyl, heteroaralkylcarbonyloxy, amino and amido; or $R^5$ when bonded to a carbon substituted with an $R^4$ may optionally be, taken together with the $R^4$, an oxo.

In certain embodiments, the invention relates to any of the aforementioned compounds and attendant definitions, provided the compound is not

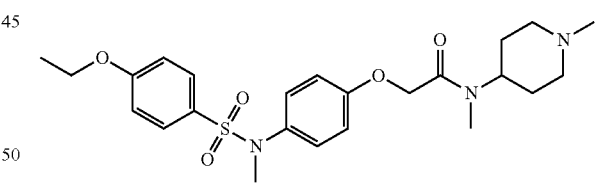

In certain embodiments, the invention relates to any of the aforementioned compounds and attendant definitions, wherein

is 1,4-phenyl diradical, 1,3-phenyl diradical, 1,2-phenyl diradical, 2,5-pyridyl diradical, 2,4-pyridyl diradical, 2,3-pyridyl diradical, 3,4-pyridyl diradical, or 3,5-pyridyl diradical.

In certain embodiments, the invention relates to any of the aforementioned compounds and attendant definitions, wherein is 1,4-phenyl diradical or 2,5-pyridyl diradical. In certain embodiments, the invention relates to any of the aforementioned compounds and attendant definitions, wherein

is 1,4-phenyl diradical.

In certain embodiments, the invention relates to any of the aforementioned compounds and attendant definitions, wherein $R^1$ is

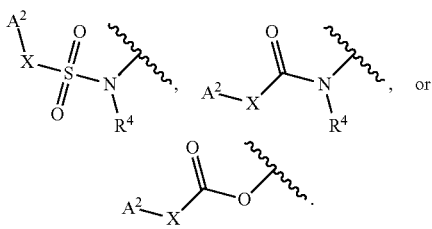

In certain embodiments, the invention relates to any of the aforementioned compounds and attendant definitions, wherein $R^1$ is

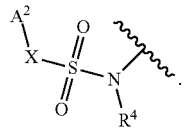

In certain embodiments, the invention relates to any of the aforementioned compounds and attendant definitions, wherein $R^2$ is

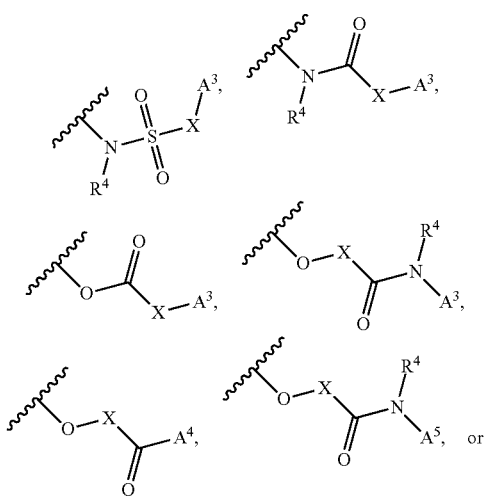

-continued

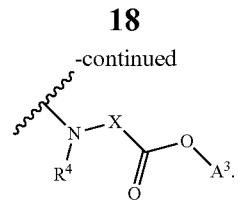

In certain embodiments, the invention relates to any of the aforementioned compounds and attendant definitions, wherein $R^2$ is

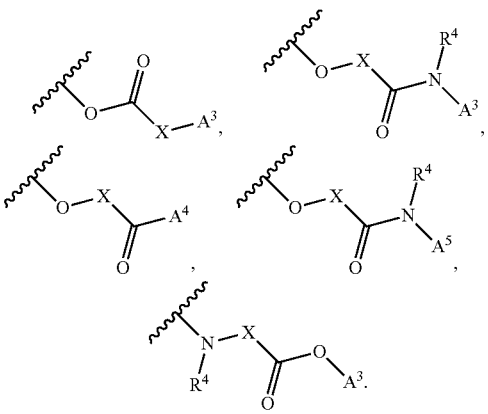

In certain embodiments, the invention relates to any of the aforementioned compounds and attendant definitions, wherein $R^2$ is

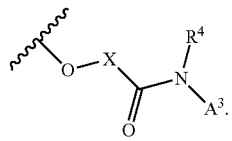

In certain embodiments, the invention relates to any of the aforementioned compounds and attendant definitions, wherein $R^2$ is

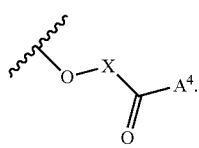

In certain embodiments, the invention relates to any of the aforementioned compounds and attendant definitions, wherein $R^2$ is

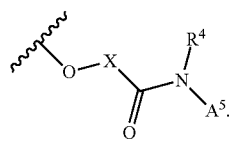

In certain embodiments, the invention relates to any of the aforementioned compounds and attendant definitions, wherein $A^2$ is substituted or unsubstituted phenyl or pyridyl.

In certain embodiments, the invention relates to any of the aforementioned compounds and attendant definitions, wherein A² is substituted phenyl or substituted pyridyl. In certain embodiments, the invention relates to any of the aforementioned compounds and attendant definitions, wherein A² is 4-substituted phenyl. In certain embodiments, the invention relates to any of the aforementioned compounds and attendant definitions, wherein A² is 4-alkyoxyphenyl. In certain embodiments, the invention relates to any of the aforementioned compounds and attendant definitions, wherein A² is 4-ethoxyphenyl.

In certain embodiments, the invention relates to any of the aforementioned compounds and attendant definitions, wherein A³ is substituted or unsubstituted cyclopentyl, cyclohexyl, piperidyl, pyrrolidyl, or tetrahydro-2H-pyranyl. In certain embodiments, the invention relates to any of the aforementioned compounds and attendant definitions, wherein A³ is substituted cyclopentyl, substituted cyclohexyl, substituted piperidyl, substituted pyrrolidyl, or substituted tetrahydro-2H-pyranyl. In certain embodiments, the invention relates to any of the aforementioned compounds and attendant definitions, wherein A³ is 4-alkylcyclohexyl or 1-alkyl-4-piperidyl. In certain embodiments, the invention relates to any of the aforementioned compounds and attendant definitions, wherein A³ is 4-methylcyclohexyl or 1-methyl-4-piperidyl.

In certain embodiments, the invention relates to any of the aforementioned compounds and attendant definitions, wherein A³ is 1-aralkyl-3-pyrrolidyl. In certain embodiments, the invention relates to any of the aforementioned compounds and attendant definitions, wherein A³ is 1-benzyl-3-pyrrolidyl. In certain embodiments, the invention relates to any of the aforementioned compounds and attendant definitions, wherein A³ comprises a nitrogen atom.

In certain embodiments, the invention relates to any of the aforementioned compounds and attendant definitions, wherein A⁴ is a substituted five-, six-, or seven-membered heterocycloalkyl ring. In certain embodiments, the invention relates to any of the aforementioned compounds and attendant definitions, wherein A⁴ is substituted or unsubstituted piperidyl, pyrrolidyl, diazepyl, or tetrahydro-2H-pyranyl. In certain embodiments, the invention relates to any of the aforementioned compounds and attendant definitions, wherein A⁴ is substituted piperidyl, substituted pyrrolidyl, or substituted diazepyl. In certain embodiments, the invention relates to any of the aforementioned compounds and attendant definitions, wherein A⁴ is 4-benzyl-1,4-diazepyl. In certain embodiments, the invention relates to any of the aforementioned compounds and attendant definitions, wherein A⁴ is 4-acetyl-1,4-diazepyl. In certain embodiments, the invention relates to any of the aforementioned compounds and attendant definitions, wherein A⁴ is 3-amino-1-pyrrolidyl. In certain embodiments, the invention relates to any of the aforementioned compounds and attendant definitions, wherein A⁴ is 2-(pyrrolidylmethyl)-1-pyrrolidyl. In certain embodiments, the invention relates to any of the aforementioned compounds and attendant definitions, wherein A⁴ is 4-pyrrolidyl-1-piperidyl. In certain embodiments, the invention relates to any of the aforementioned compounds and attendant definitions, wherein A⁴ is 2-(2-pyrrolidylethyl)-1-piperidyl. In certain embodiments, the invention relates to any of the aforementioned compounds and attendant definitions, wherein A⁴ comprises at least one nitrogen atom. In certain embodiments, the invention relates to any of the aforementioned compounds and attendant definitions, wherein A⁴ comprises two nitrogen atoms.

In certain embodiments, the invention relates to any of the aforementioned compounds and attendant definitions, wherein A⁵ is an unsubstituted aralkyl moiety. In certain embodiments, the invention relates to any of the aforementioned compounds and attendant definitions, wherein A⁵ is benzyl. In certain embodiments, the invention relates to any of the aforementioned compounds and attendant definitions, wherein A⁵ is a substituted aralkyl moiety. In certain embodiments, the invention relates to any of the aforementioned compounds and attendant definitions, wherein A⁵ is 1-amino-2-phenylethyl. In certain embodiments, the invention relates to any of the aforementioned compounds and attendant definitions, wherein A⁵ comprises a nitrogen atom.

In certain embodiments, the invention relates to any of the aforementioned compounds and attendant definitions, wherein X is a bond. In certain embodiments, the invention relates to any of the aforementioned compounds and attendant definitions, wherein X is

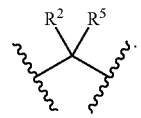

In certain embodiments, the invention relates to any of the aforementioned compounds and attendant definitions, wherein X is

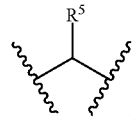

In certain embodiments, the invention relates to any of the aforementioned compounds and attendant definitions, wherein X is

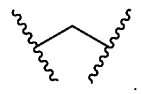 [SMILES: *C*]

In certain embodiments, the invention relates to any of the aforementioned compounds and attendant definitions, wherein X is

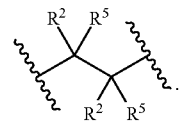

In certain embodiments, the invention relates to any of the aforementioned compounds and attendant definitions, wherein X

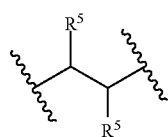

In certain embodiments, the invention relates to any of the aforementioned compounds and attendant definitions, wherein X is

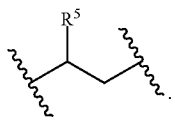

In certain embodiments, the invention relates to any of the aforementioned compounds and attendant definitions, wherein R³ is hydrogen, alkyl or aryl. In certain embodiments, the invention relates to any of the aforementioned compounds and attendant definitions, wherein R³ is hydrogen.

In certain embodiments, the invention relates to any of the aforementioned compounds and attendant definitions, wherein R⁴ is hydrogen, alkyl, aralkyl, alkylcarbonyl or aralkylcarbonyl. In certain embodiments, the invention relates to any of the aforementioned compounds and attendant definitions, wherein R⁴ is hydrogen. In certain embodiments, the invention relates to any of the aforementioned compounds and attendant definitions, wherein R⁴ is alkyl. In certain embodiments, the invention relates to any of the aforementioned compounds and attendant definitions, wherein R⁴ is methyl.

In certain embodiments, the invention relates to any of the aforementioned compounds and attendant definitions, wherein R⁵ is hydrogen.

In certain embodiments, the invention relates to any of the aforementioned compounds and attendant definitions, wherein R⁵ is alkyl. In certain embodiments, the invention relates to any of the aforementioned compounds and attendant definitions, wherein R⁵ is methyl, ethyl, n-propyl, iso-propyl, n-butyl, sec-butyl, or iso-butyl.

Another aspect of the invention relates to a subset of compounds of formula I which are represented by formula II:

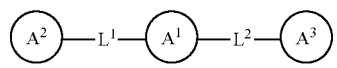

or a pharmaceutically acceptable salt, solvate, hydrate, pro-drug, chemically-protected form, enantiomer or stereoisomer thereof; wherein, independently for each occurrence,

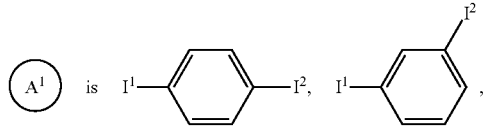

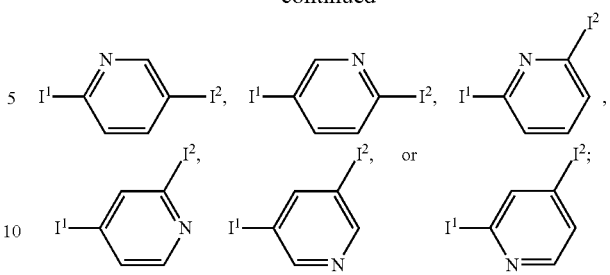

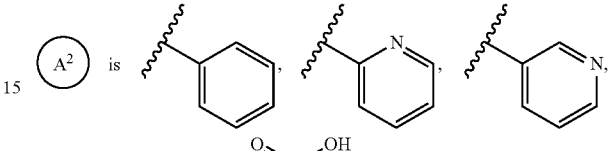

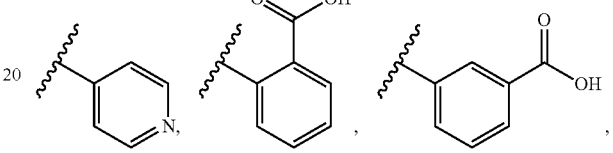

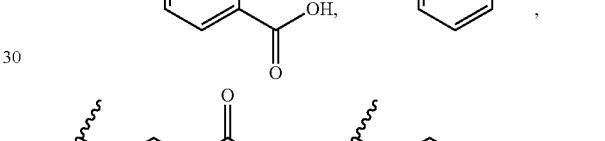

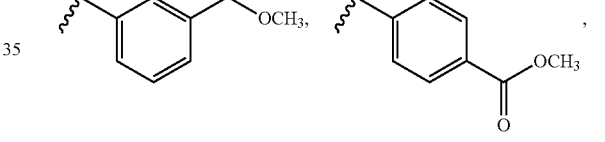

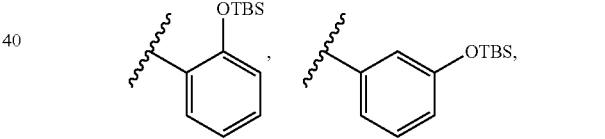

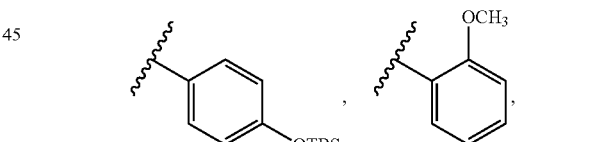

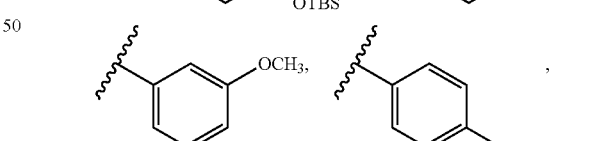

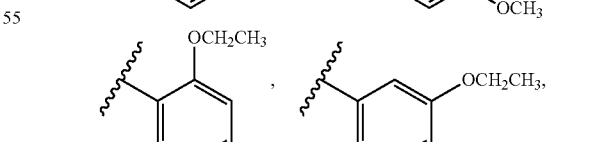

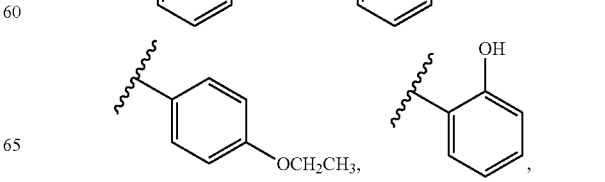

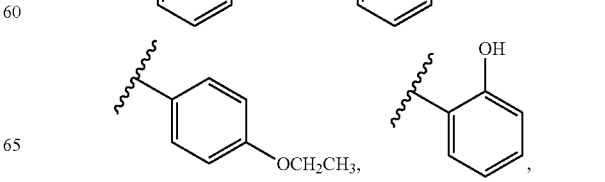

23
-continued
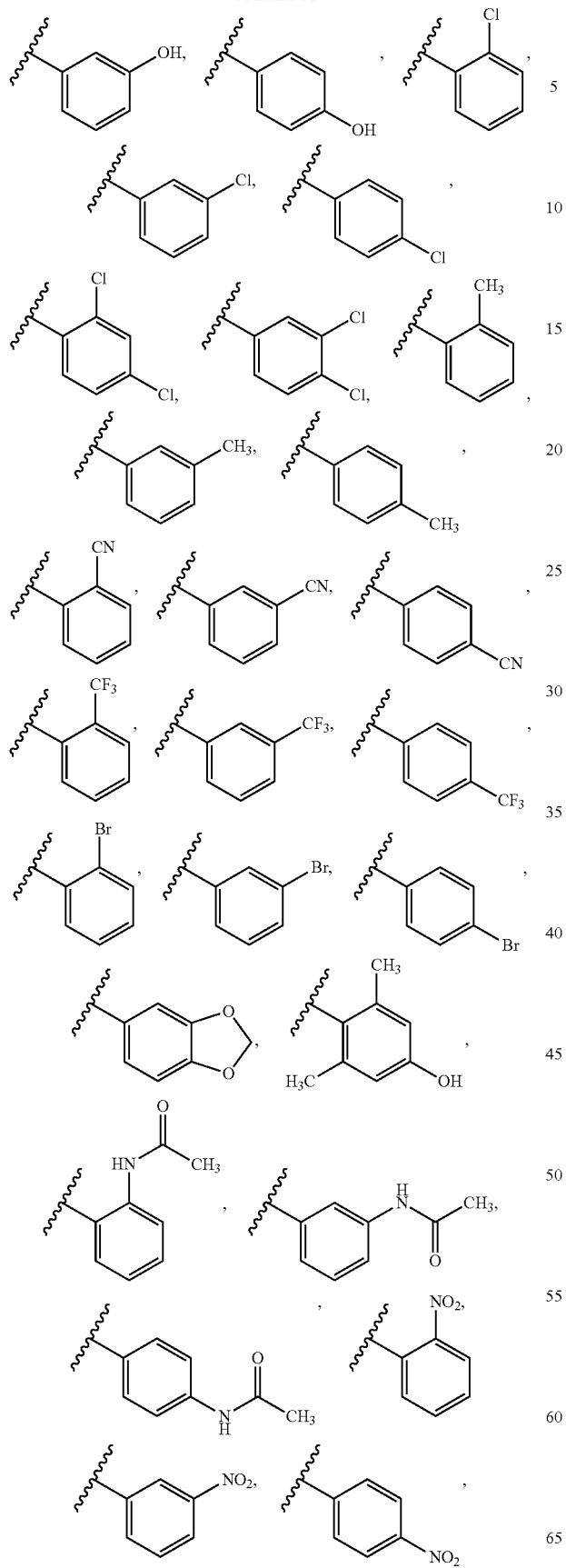
24
-continued
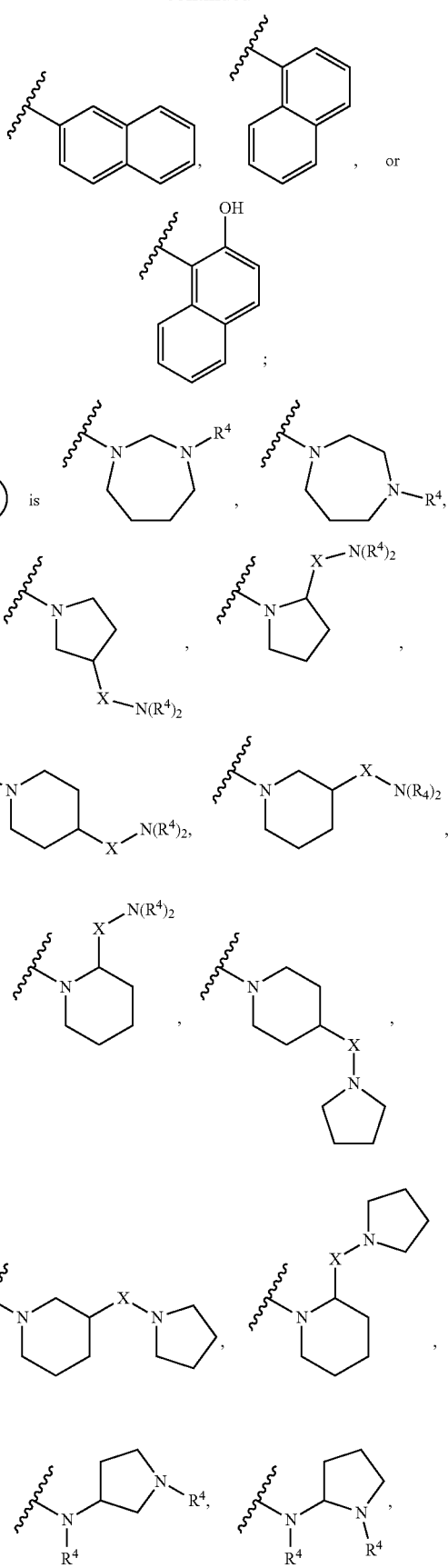

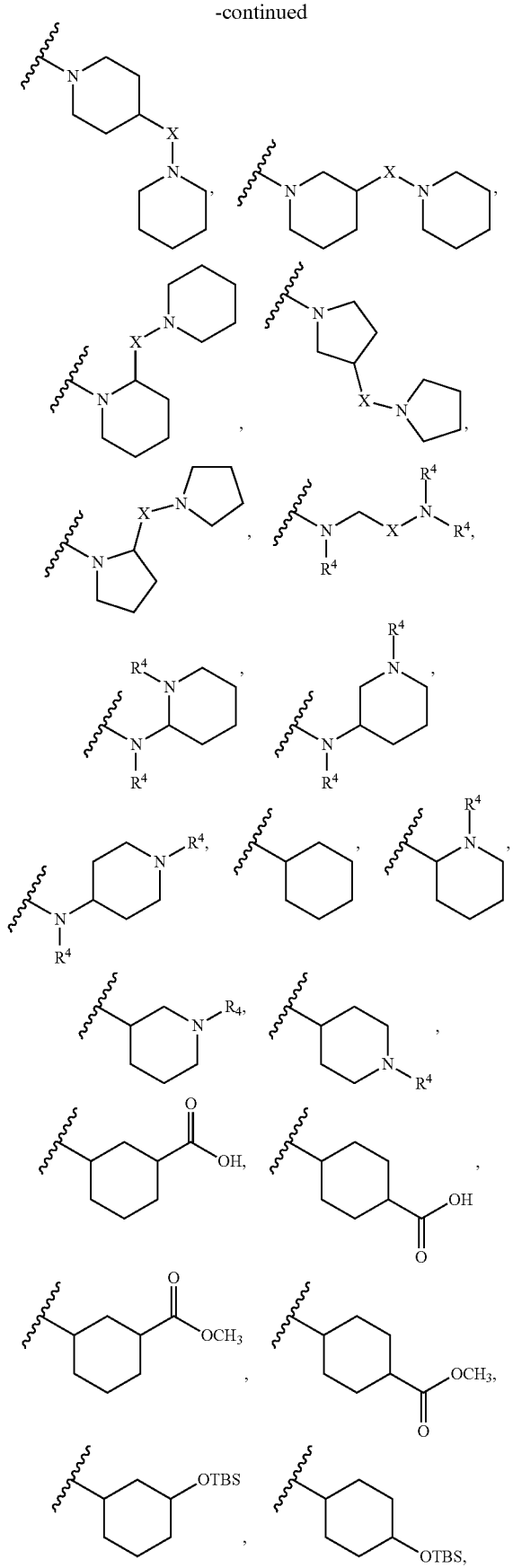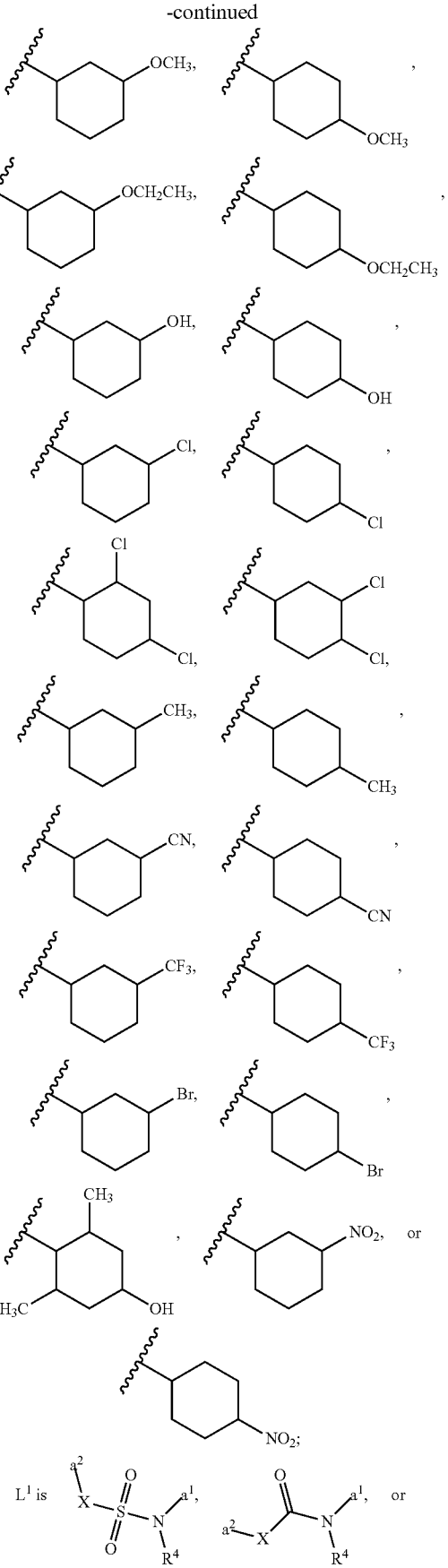

-continued

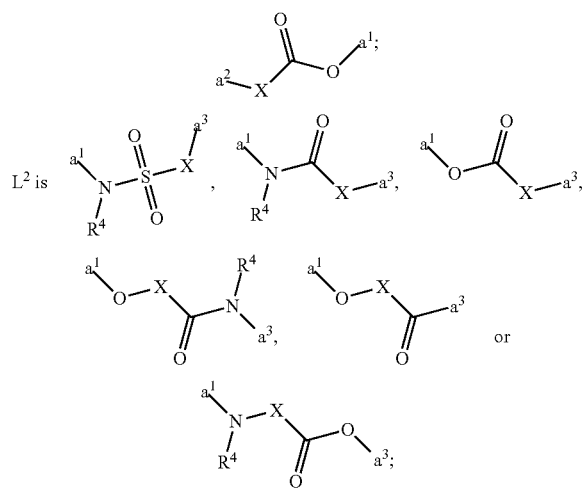

l¹ is a bond to L¹;
l² is a bond to L²;
a¹ is a bond to

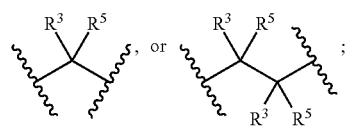

X is a bond,

R³ is hydrogen or alkyl;
R⁴ is hydrogen, alkyl, aralkyl, or alkylcarbonyl; and
R⁵ is hydrogen, or alkyl, haloalkyl, or alkyl substituted with hydroxy, cyano, carboxy, aralkyloxy, alkyloxycarbonyl or aralkyloxycarbonyl.

In certain embodiments, the invention relates to any of the aforementioned compounds and attendant definitions, provided the compound is not

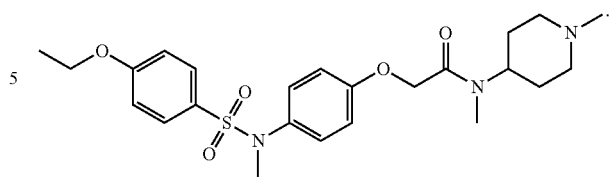

In certain embodiments, the invention relates to any of the aforementioned compounds and attendant definitions, wherein

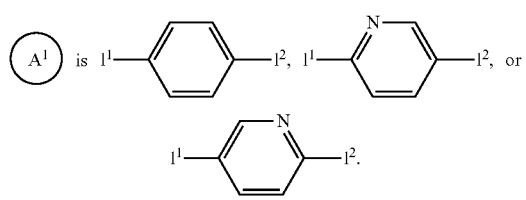

In certain embodiments, the invention relates to any of the aforementioned compounds and attendant definitions, wherein

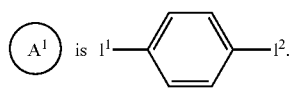

In certain embodiments, the invention relates to any of the aforementioned compounds and attendant definitions, wherein

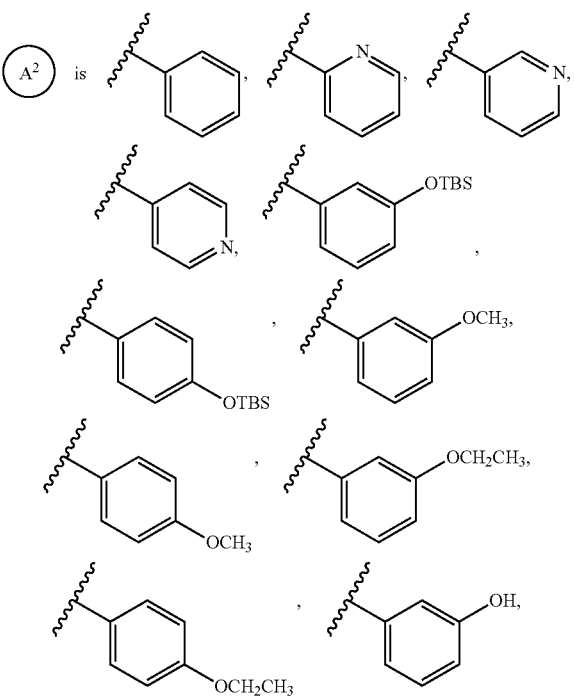

In certain embodiments, the invention relates to any of the aforementioned compounds and attendant definitions, wherein

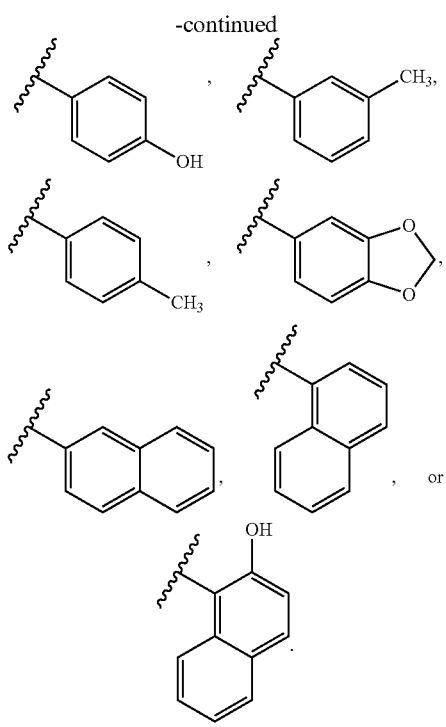

In certain embodiments, the invention relates to any of the aforementioned compounds and attendant definitions, wherein

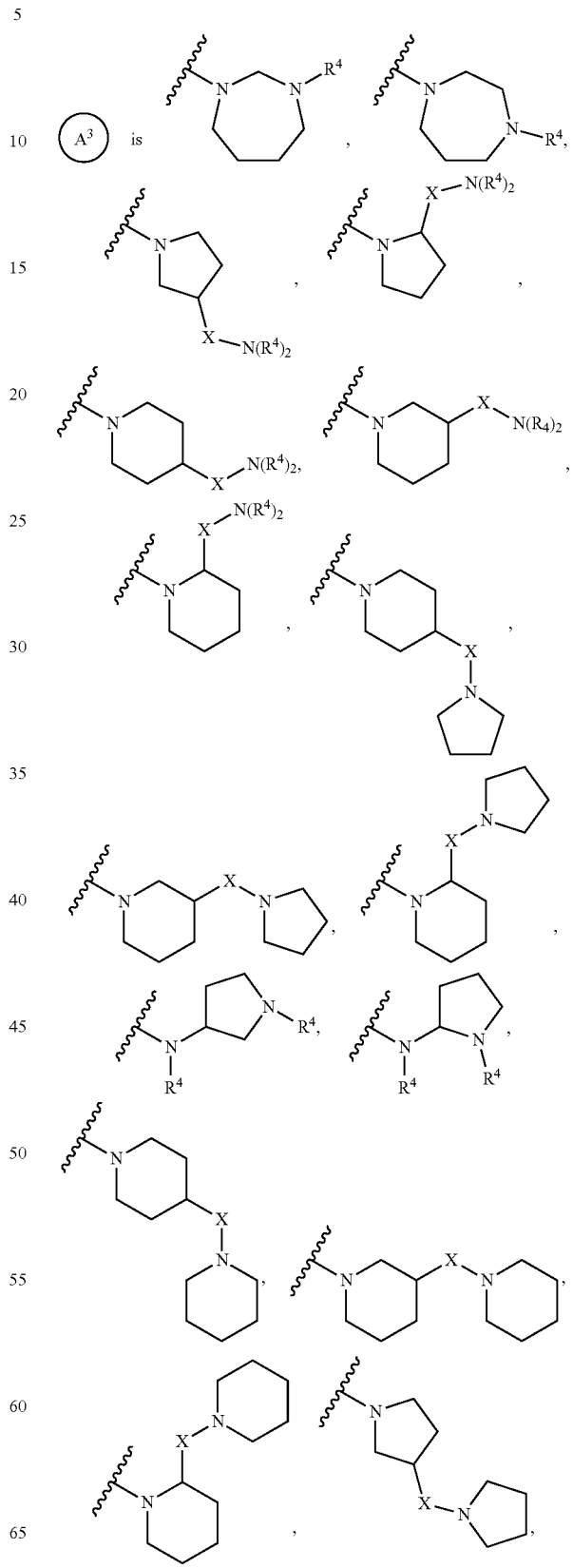

In certain embodiments, the invention relates to any of the aforementioned compounds and attendant definitions, wherein A³ comprises at least two nitrogen atoms.

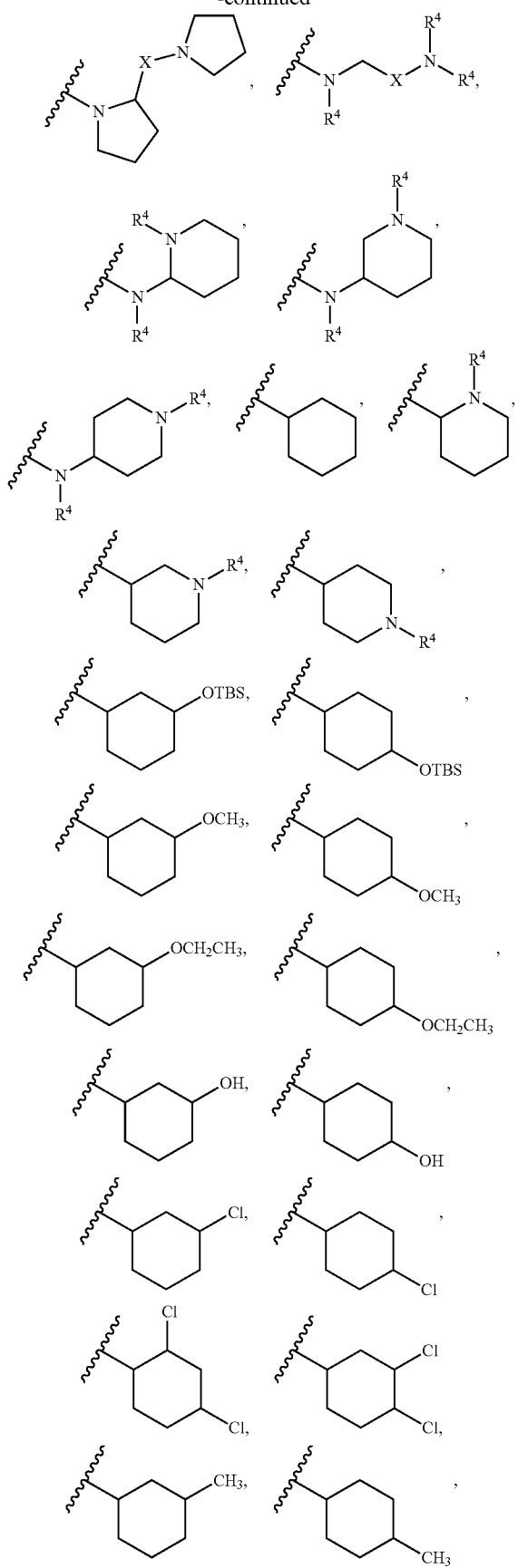
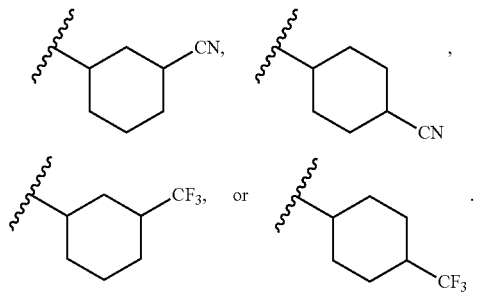
In certain embodiments, the invention relates to any of the aforementioned compounds and attendant definitions, wherein
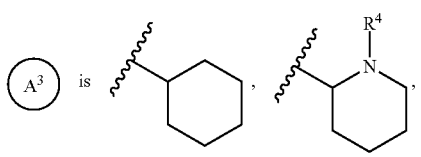
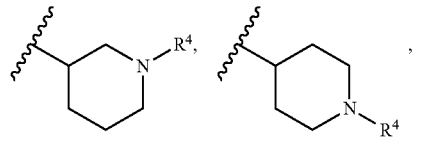
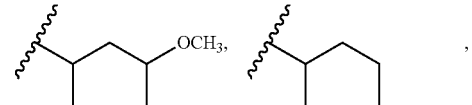
In certain embodiments, the invention relates to any of the aforementioned compounds and attendant definitions, wherein
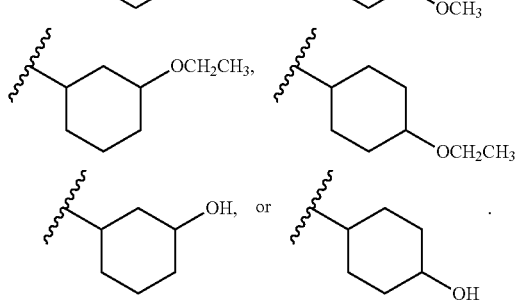
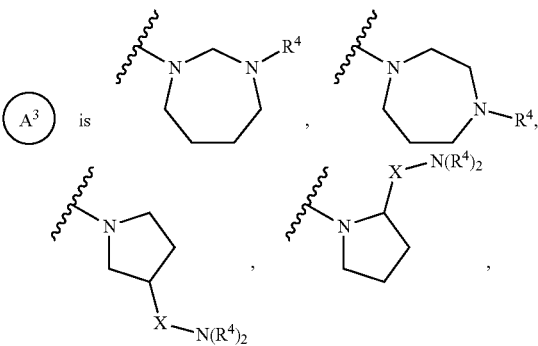

-continued

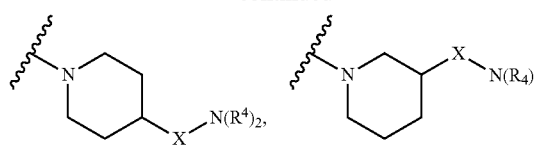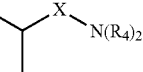

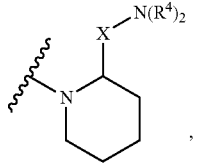

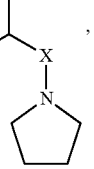

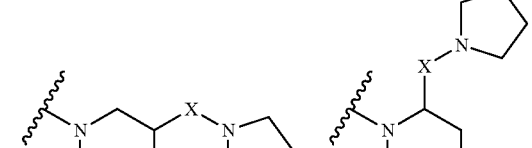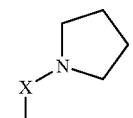

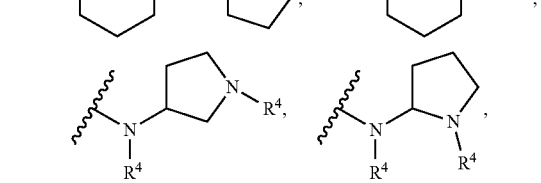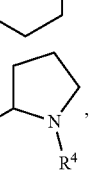

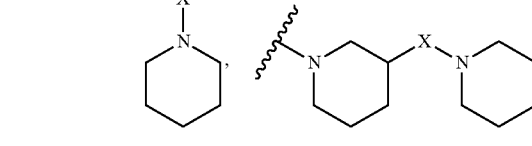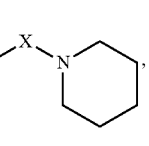

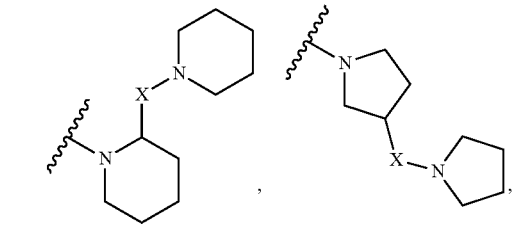

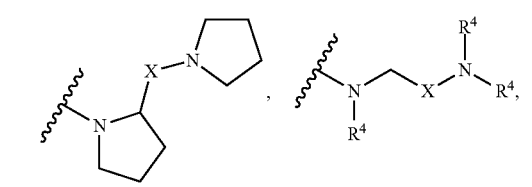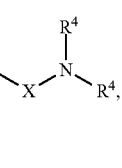

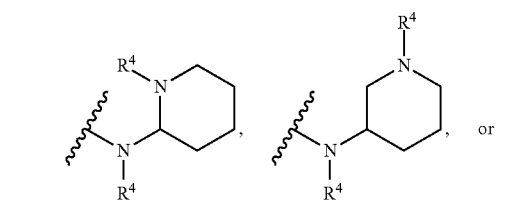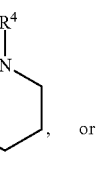 or

-continued

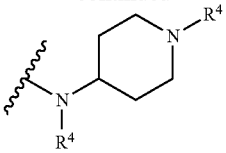

In certain embodiments, the invention relates to any of the aforementioned compounds and attendant definitions, wherein $L^1$ is

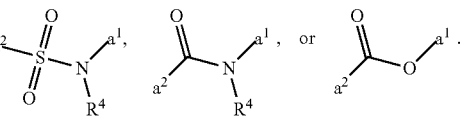

In certain embodiments, the invention relates to any of the aforementioned compounds and attendant definitions, wherein $L^1$ is

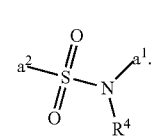

In certain embodiments, the invention relates to any of the aforementioned compounds and attendant definitions, wherein $L^2$ is

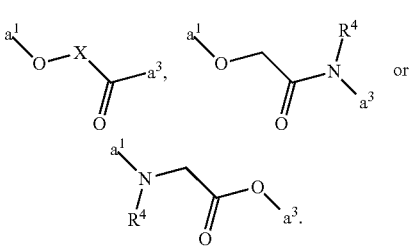

In certain embodiments, the invention relates to any of the aforementioned compounds and attendant definitions, wherein $L^2$ is

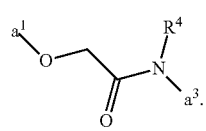

In certain embodiments, the invention relates to any of the aforementioned compounds and attendant definitions, wherein $L^2$ is

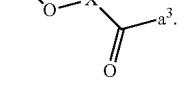

In certain embodiments, the invention relates to any of the aforementioned compounds and attendant definitions, wherein $L^2$ is

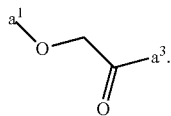

In certain embodiments, the invention relates to any of the aforementioned compounds and attendant definitions, wherein X is a bond. In certain embodiments, the invention relates to any of the aforementioned compounds and attendant definitions, wherein X is

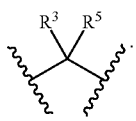

In certain embodiments, the invention relates to any of the aforementioned compounds and attendant definitions, wherein X is

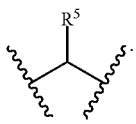

In certain embodiments, the invention relates to any of the aforementioned compounds and attendant definitions, wherein X is

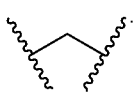

In certain embodiments, the invention relates to any of the aforementioned compounds and attendant definitions, wherein X is

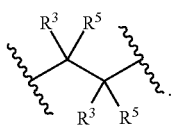

In certain embodiments, the invention relates to any of the aforementioned compounds and attendant definitions, wherein X

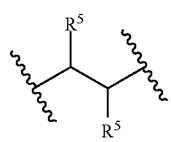

In certain embodiments, the invention relates to any of the aforementioned compounds and attendant definitions, wherein X is

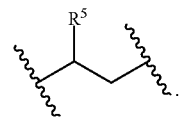

In certain embodiments, the invention relates to any of the aforementioned compounds and attendant definitions, wherein X is

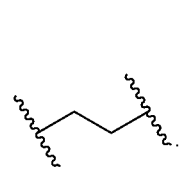 [SMILES: *CC*]

In certain embodiments, the invention relates to any of the aforementioned compounds and attendant definitions, wherein $R^3$ is hydrogen, methyl, ethyl, n-propyl, iso-propyl, n-butyl, sec-butyl, or iso-butyl. In certain embodiments, the invention relates to any of the aforementioned compounds and attendant definitions, wherein $R^3$ is hydrogen.

In certain embodiments, the invention relates to any of the aforementioned compounds and attendant definitions, wherein $R^4$ is hydrogen. In certain embodiments, the invention relates to any of the aforementioned compounds and attendant definitions, wherein $R^4$ is alkyl. In certain embodiments, the invention relates to any of the aforementioned compounds and attendant definitions, wherein $R^4$ is methyl. In certain embodiments, the invention relates to any of the aforementioned compounds and attendant definitions, wherein $R^4$ is aralkyl. In certain embodiments, the invention relates to any of the aforementioned compounds and attendant definitions, wherein $R^4$ is benzyl. In certain embodiments, the invention relates to any of the aforementioned compounds and attendant definitions, wherein $R^4$ is alkylcarbonyl. In certain embodiments, the invention relates to any of the aforementioned compounds and attendant definitions, wherein $R^4$ is acetyl. In certain embodiments, the invention relates to any of the aforementioned compounds and attendant definitions, wherein $R^4$ is ethyl.

In certain embodiments, the invention relates to any of the aforementioned compounds and attendant definitions, wherein $R^5$ is hydrogen, methyl, ethyl, n-propyl, iso-propyl, n-butyl, sec-butyl, or iso-butyl. In certain embodiments, the invention relates to any of the aforementioned compounds and attendant definitions, wherein $R^5$ is hydrogen.

In certain embodiments, the invention relates to any of the aforementioned compounds and attendant definitions, wherein the compound is selected from the group consisting of

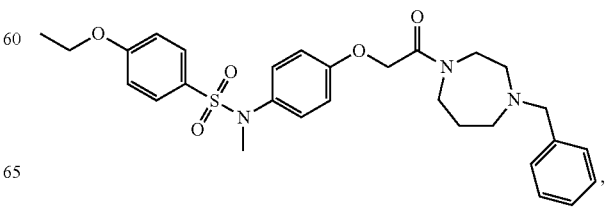

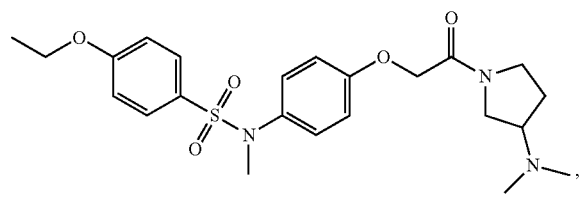
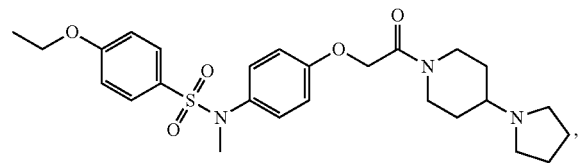
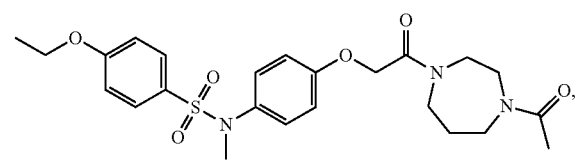
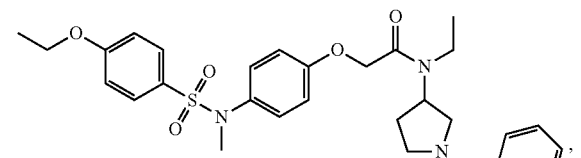
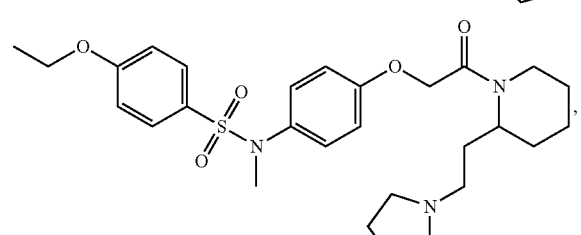
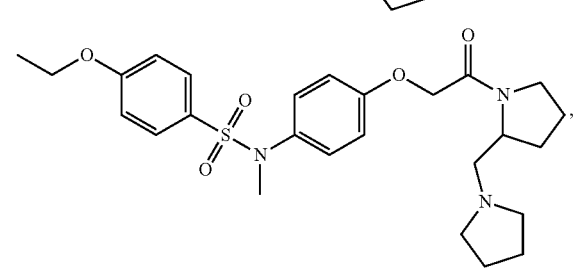
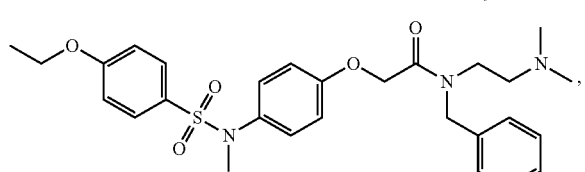
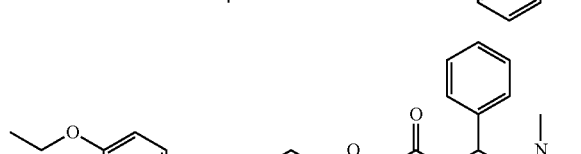
and
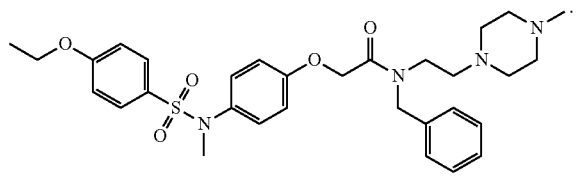
One aspect of the invention relates to a compound represented by formula III:
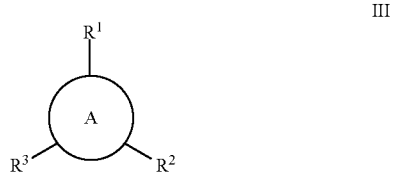
or a pharmaceutically acceptable salt, solvate, hydrate, prodrug, chemically-protected form, enantiomer or stereoisomer thereof; wherein, independently for each occurrence,
is a five-membered saturated or unsaturated heterocycloalkyl triradical;
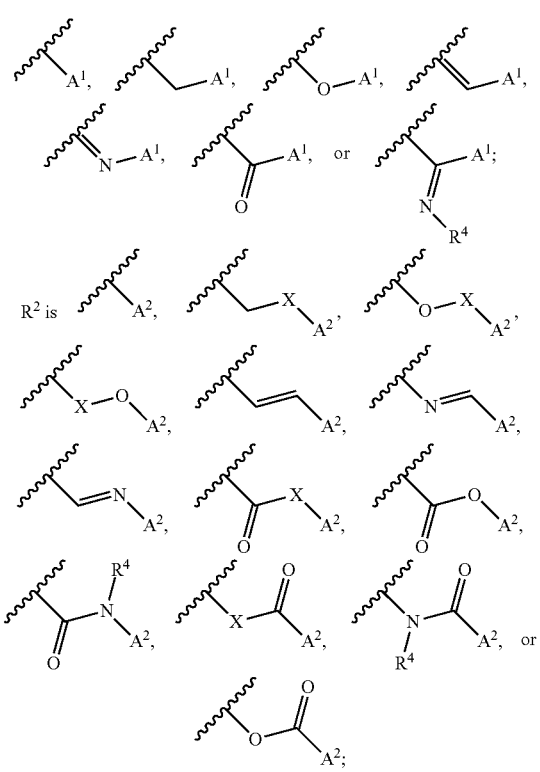

R³ is

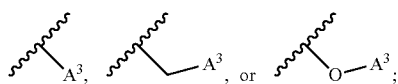

A¹ is a substituted or unsubstituted six-membered aryl or heteroaryl ring;
A² is a substituted or unsubstituted six-membered aryl or heteroaryl ring;
A³ is a substituted or unsubstituted five-membered heteroaryl ring;
X is a bond,

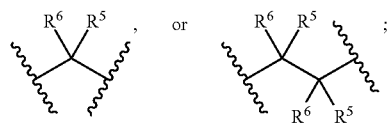

R⁴ is hydrogen, alkyl, haloalkyl, aryl, heteroaryl, aralkyl, heteroaralkyl, alkylcarbonyl, haloalkyl, arylcarbonyl, heteroarylcarbonyl, aralkylcarbonyl or heteroaralkylcarbonyl;
R⁵ is hydrogen, alkyl, haloalkyl or alkyl substituted with one or two substituents independently selected from the group consisting of halo, cyano, haloalkyl, carbocyclyl, heterocyclyl, aryl, heteroaryl, carbocyclylalkyl, heterocyclylalkyl, aralkyl, heteroaralkyl, hydroxy, alkyloxy, haloalkyloxy, carbocyclyloxy, heterocyclyloxy, aryloxy, heteroaryloxy, carbocyclylalkyloxy, heterocyclylalkyloxy, aralkyloxy, heteroaralkyloxy, alkylcarbonyloxy, halo alkylcarbonyloxy, carbocyclylcarbonyloxy, heterocyclylcarbonyloxy, arylcarbonyloxy, heteroarylcarbonyloxy, carbocyclylalkylcarbonyloxy, heterocyclylalkylcarbonyloxy, aralkylcarbonyloxy, heteroaralkylcarbonyloxy, carboxy, alkyloxycarbonyl, halo alkyloxycarbonyl, carbocyclyloxycarbonyl, heterocyclyloxycarbonyl, aryloxycarbonyl, heteroaryloxycarbonyl, carbocyclylalkyloxycarbonyl, heterocyclylalkyloxycarbonyl, aralkyloxycarbonyl, heteroaralkylcarbonyloxy, amino and amido; or R⁵ when bonded to a carbon substituted with an R⁴ may optionally be, taken together with the R⁴, an oxo; and
R⁶ is hydrogen, halo, alkyl or haloalkyl.
In certain embodiments, the invention relates to any of the aforementioned compounds and attendant definitions, provided the compound is not

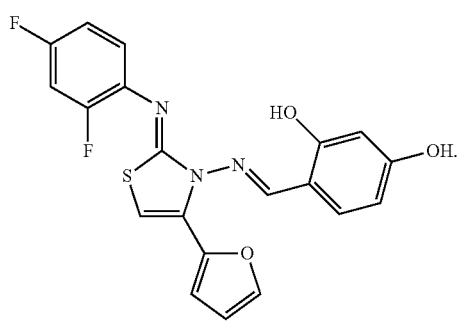 [SMILES: Oc1ccc(/C=N/n2c(-c3ccco3)cs/c2=N\c2ccc(F)cc2F)c(O)c1]

In certain embodiments, the invention relates to any of the aforementioned compounds and attendant definitions, wherein

is five-membered unsaturated heterocycloalkyl triradical. In certain embodiments, the invention relates to any of the aforementioned compounds and attendant definitions, wherein

is five-membered unsaturated heterocycloalkyl triradical, wherein the five-membered unsaturated heterocycloalkyl triradical comprises at least one sulfur moiety. In certain embodiments, the invention relates to any of the aforementioned compounds and attendant definitions, wherein

is five-membered unsaturated heterocycloalkyl triradical, wherein the five-membered unsaturated heterocycloalkyl triradical comprises at least one oxygen moiety. In certain embodiments, the invention relates to any of the aforementioned compounds and attendant definitions, wherein

is five-membered unsaturated heterocycloalkyl triradical, wherein the five-membered unsaturated heterocycloalkyl triradical comprises at least one sulfur moiety and at least one nitrogen moiety. In certain embodiments, the invention relates to any of the aforementioned compounds and attendant definitions, wherein

is five-membered unsaturated heterocycloalkyl triradical, wherein the five-membered unsaturated heterocycloalkyl triradical comprises at least one oxygen moiety and at least one nitrogen moiety. In certain embodiments, the invention relates to any of the aforementioned compounds and attendant definitions, wherein

 is 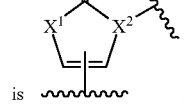, wherein X¹ is sulfur or oxygen; and X² is nitrogen or —CR⁴.

In certain embodiments, the invention relates to any of the aforementioned compounds and attendant definitions, wherein $R^1$ is

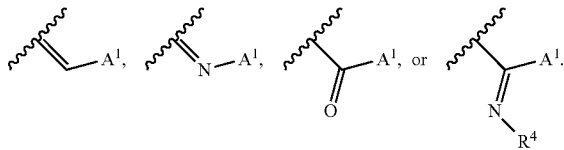

In certain embodiments, the invention relates to any of the aforementioned compounds and attendant definitions, wherein $R^1$ is

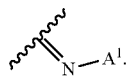

In certain embodiments, the invention relates to any of the aforementioned compounds and attendant definitions, wherein $R^2$ is

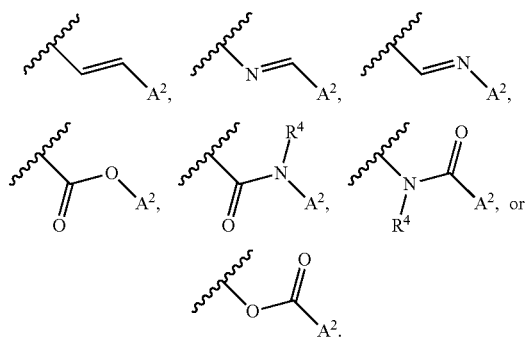

In certain embodiments, the invention relates to any of the aforementioned compounds and attendant definitions, wherein $R^2$ is

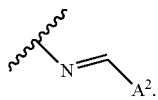

In certain embodiments, the invention relates to any of the aforementioned compounds and attendant definitions, wherein $R^3$ is

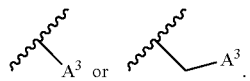

In certain embodiments, the invention relates to any of the aforementioned compounds and attendant definitions, wherein $R^3$ is

In certain embodiments, the invention relates to any of the aforementioned compounds and attendant definitions, wherein $A^1$ is substituted or unsubstituted phenyl or pyridyl. In certain embodiments, the invention relates to any of the aforementioned compounds and attendant definitions, wherein $A^1$ is substituted phenyl or substituted pyridyl. In certain embodiments, the invention relates to any of the aforementioned compounds and attendant definitions, wherein $A^1$ is 2-substituted phenyl, 4-substituted phenyl, or 2,4-disubstituted phenyl. In certain embodiments, the invention relates to any of the aforementioned compounds and attendant definitions, wherein $A^1$ is 2,4-disubstituted phenyl, wherein the substituents are the same or different. In certain embodiments, the invention relates to any of the aforementioned compounds and attendant definitions, wherein $A^1$ is 2,4-dihalophenyl. In certain embodiments, the invention relates to any of the aforementioned compounds and attendant definitions, wherein $A^1$ is 2,4-difluorophenyl.

In certain embodiments, the invention relates to any of the aforementioned compounds and attendant definitions, wherein $A^2$ is substituted or unsubstituted phenyl or pyridyl. In certain embodiments, the invention relates to any of the aforementioned compounds and attendant definitions, wherein $A^2$ is substituted phenyl or substituted pyridyl. In certain embodiments, the invention relates to any of the aforementioned compounds and attendant definitions, wherein $A^2$ is 2-substituted phenyl, 4-substituted phenyl, or 2,4-disubstituted phenyl. In certain embodiments, the invention relates to any of the aforementioned compounds and attendant definitions, wherein $A^2$ is 2,4-disubstituted phenyl, wherein the substituents are the same or different. In certain embodiments, the invention relates to any of the aforementioned compounds and attendant definitions, wherein $A^2$ is 2,4-dihydroxyphenyl.

In certain embodiments, the invention relates to any of the aforementioned compounds and attendant definitions, wherein $A^3$ is substituted or unsubstituted pyrrole, thiophene, furan, imidazole, oxazole, or thiazole. In certain embodiments, the invention relates to any of the aforementioned compounds and attendant definitions, wherein $A^3$ is unsubstituted pyrrole, thiophene, furan, imidazole, oxazole, or thiazole. In certain embodiments, the invention relates to any of the aforementioned compounds and attendant definitions, wherein $A^3$ is substituted or unsubstituted pyrrole, thiophene, or furan. In certain embodiments, the invention relates to any of the aforementioned compounds and attendant definitions, wherein $A^3$ is substituted or unsubstituted furan.

In certain embodiments, the invention relates to any of the aforementioned compounds and attendant definitions, wherein X is a bond. In certain embodiments, the invention relates to any of the aforementioned compounds and attendant definitions, wherein X is

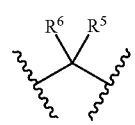

In certain embodiments, the invention relates to any of the aforementioned compounds and attendant definitions, wherein X is

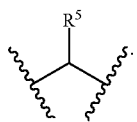

In certain embodiments, the invention relates to any of the aforementioned compounds and attendant definitions, wherein X is

In certain embodiments, the invention relates to any of the aforementioned compounds and attendant definitions, wherein X is

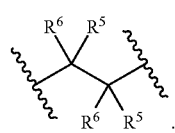

In certain embodiments, the invention relates to any of the aforementioned compounds and attendant definitions, wherein X

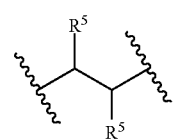

In certain embodiments, the invention relates to any of the aforementioned compounds and attendant definitions, wherein X is

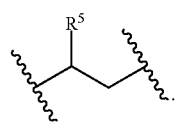

In certain embodiments, the invention relates to any of the aforementioned compounds and attendant definitions, wherein $R^4$ is hydrogen, alkyl, aralkyl, alkylcarbonyl or aralkylcarbonyl. In certain embodiments, the invention relates to any of the aforementioned compounds and attendant definitions, wherein $R^4$ is hydrogen. In certain embodiments, the invention relates to any of the aforementioned compounds and attendant definitions, wherein $R^4$ is alkyl. In certain embodiments, the invention relates to any of the aforementioned compounds and attendant definitions, wherein $R^4$ is methyl.

In certain embodiments, the invention relates to any of the aforementioned compounds and attendant definitions, wherein $R^5$ is hydrogen.

In certain embodiments, the invention relates to any of the aforementioned compounds and attendant definitions, wherein $R^5$ is alkyl. In certain embodiments, the invention relates to any of the aforementioned compounds and attendant definitions, wherein $R^5$ is methyl, ethyl, n-propyl, iso-propyl, n-butyl, sec-butyl, or iso-butyl.

In certain embodiments, the invention relates to any of the aforementioned compounds and attendant definitions, wherein $R^6$ is hydrogen, alkyl or aryl. In certain embodiments, the invention relates to any of the aforementioned compounds and attendant definitions, wherein $R^6$ is hydrogen.

Another aspect of the invention relates to a subset of compounds of formula III which are represented by formula IV:

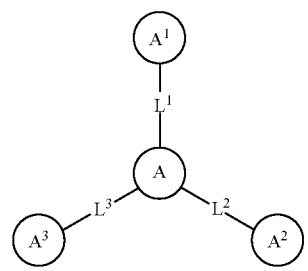

IV or a pharmaceutically acceptable salt, solvate, hydrate, prodrug, chemically-protected form, enantiomer or stereoisomer thereof; wherein, independently for each occurrence,

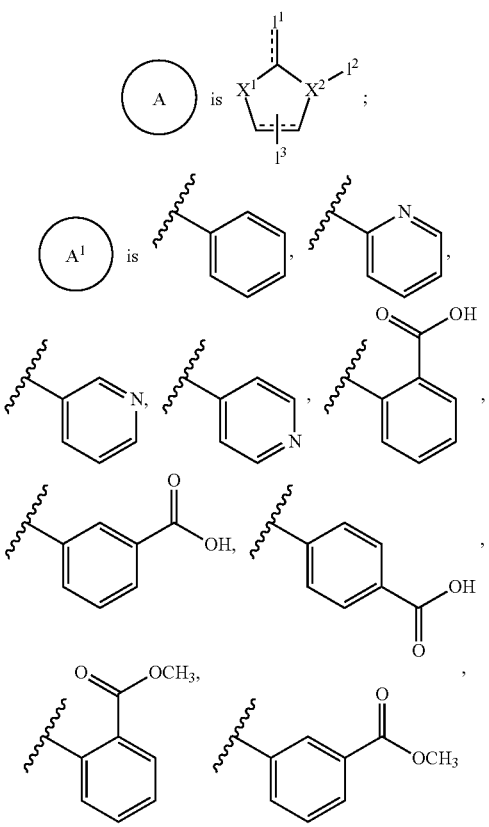

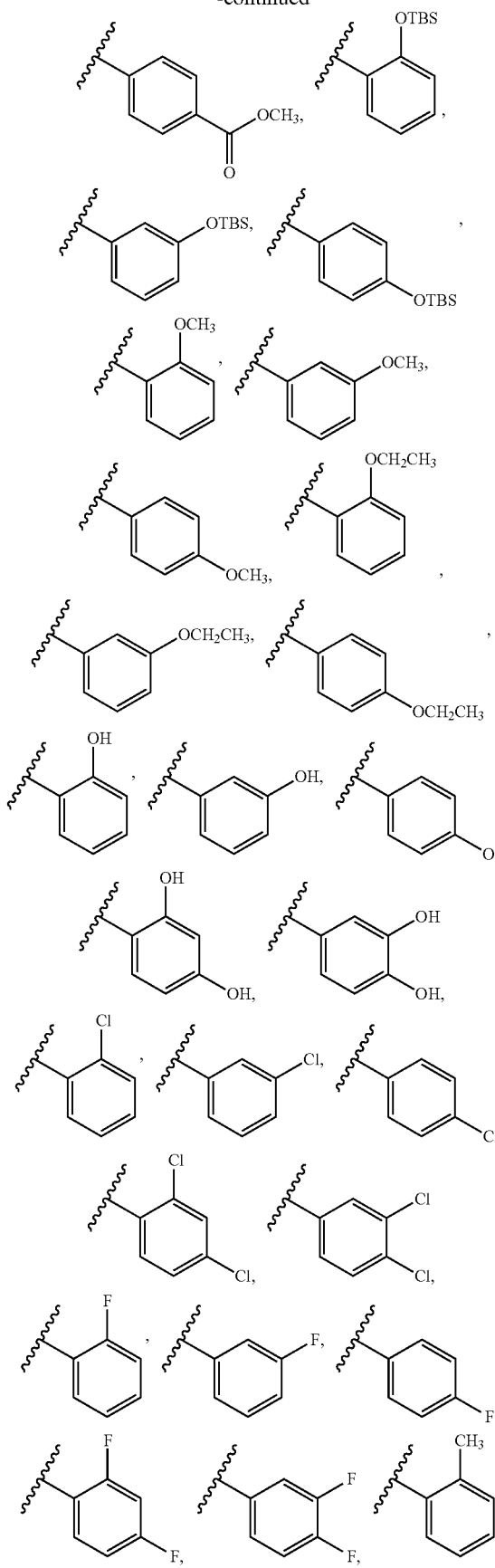
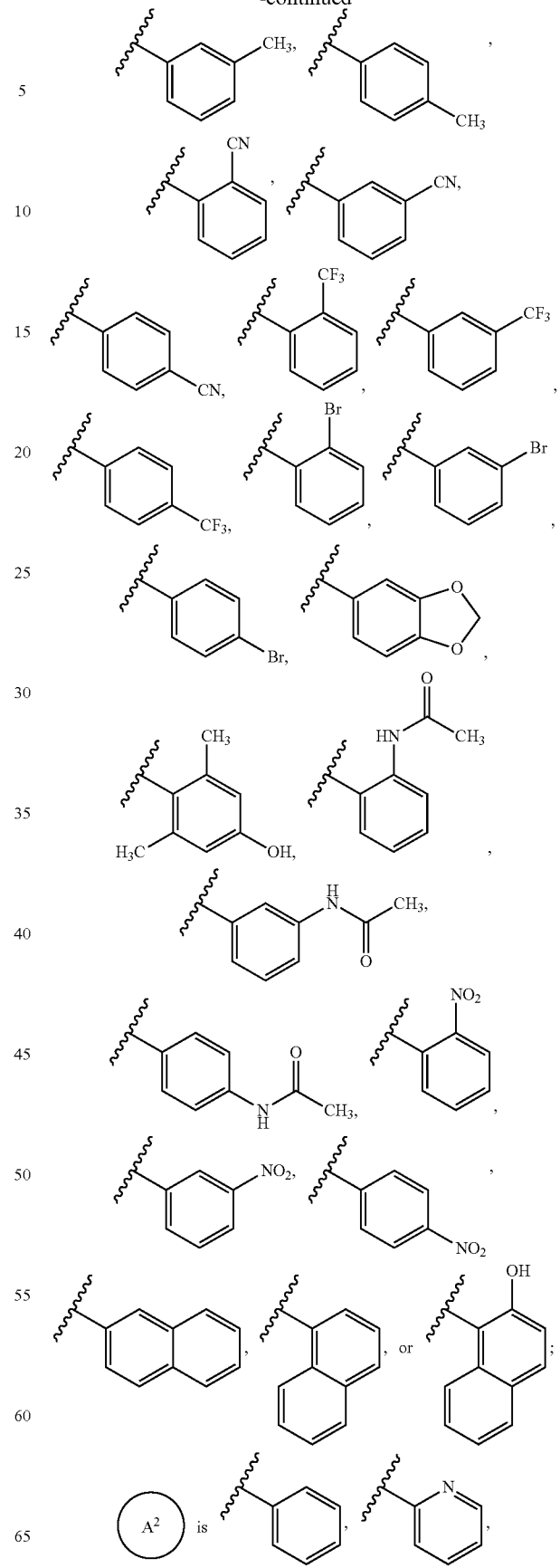

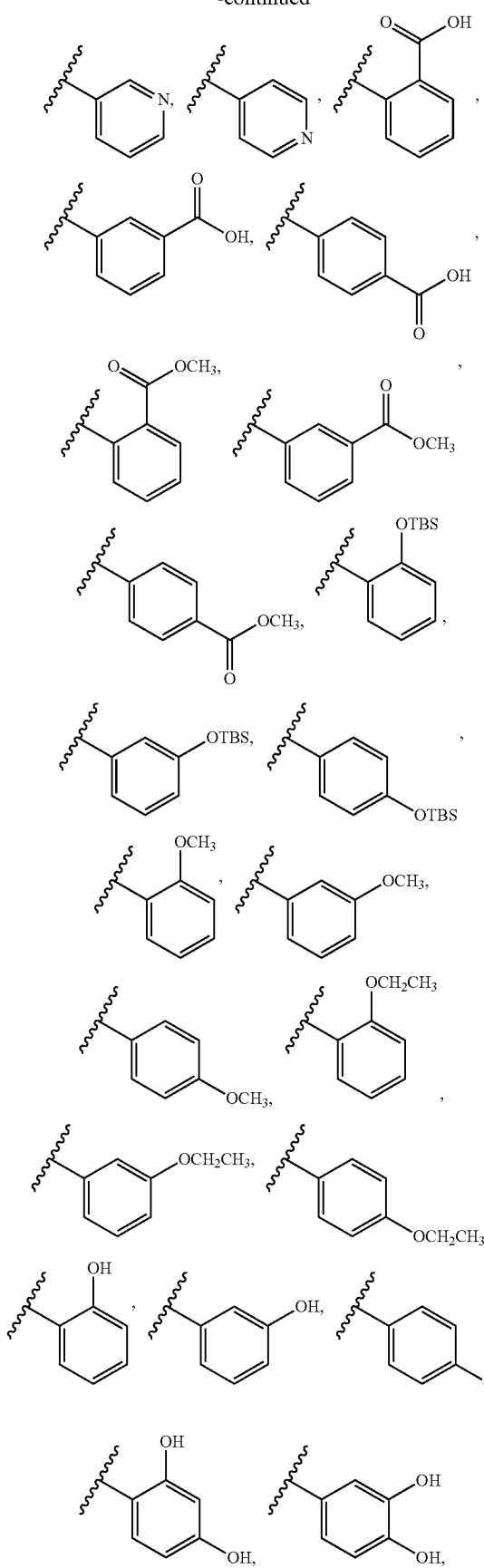
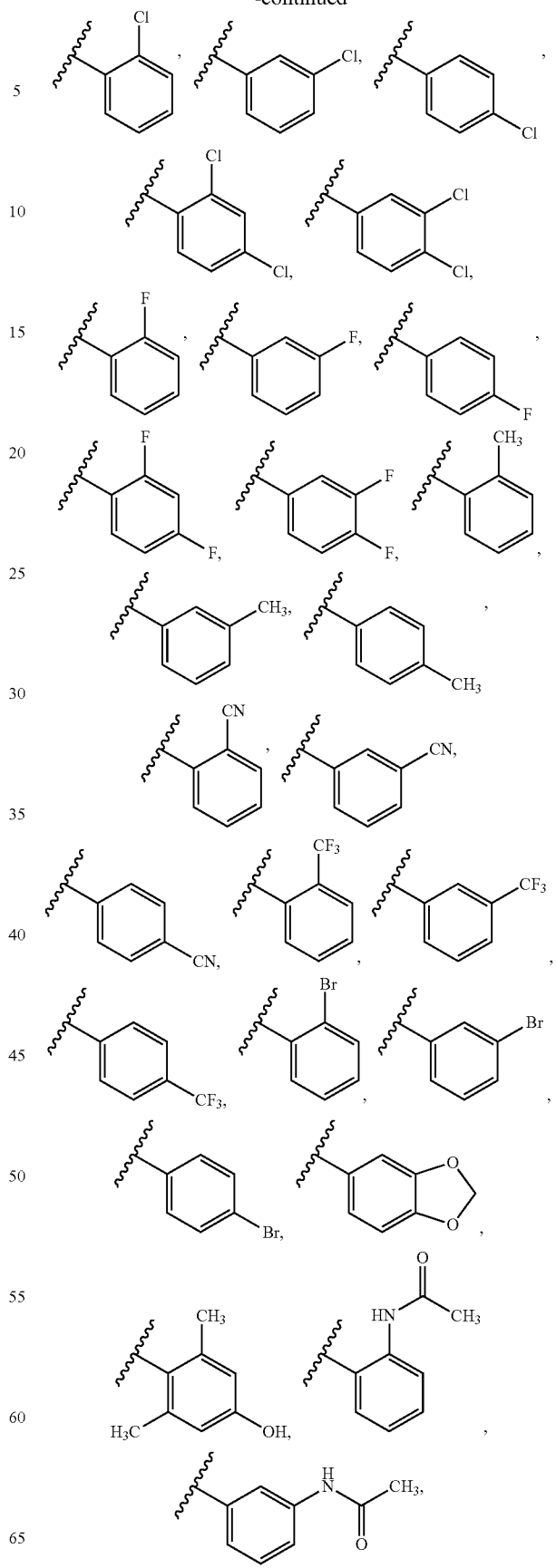

-continued

[structures: 4-acetamidophenyl; 2-nitrophenyl; 3-nitrophenyl; 4-nitrophenyl; 2-naphthyl; 1-naphthyl; 2-hydroxy-1-naphthyl]

$A^3$ is [structures: phenyl ring; N-R⁴ pyrrol-2-yl; N-R⁴ pyrrol-3-yl; N-substituted pyrrole; furan-2-yl; furan-3-yl; thiophen-2-yl, or thiophen-3-yl];

$L^1$ is

[structures: a−CH=CH−a¹, a−N=N−a¹, a−C(O)−a¹, or a−C(=NR⁴)−a¹];

$L^2$ is

[structures: a−CH=CH−a², a−N=CH−a², a−CH=N−a², a−C(O)−O−a², a−C(O)−N(R⁴)−a², a−N(R⁴)−C(O)−a², or a−O−C(O)−a²];

$L^3$ is a bond or

[structure: a−CH₂−CH₂−a³];

$X^1$ is O, S, or $NR^4$;
$X^2$ is $CR^4$ or N;
$l^1$ is a bond to $L^1$;
$l^2$ is a bond to $L^2$;
$l^3$ is a bond to $L^3$;
a is a bond to (A);

$a^1$ is a bond to (A¹);

$a^2$ is a bond to (A²);

$a^3$ is a bond to (A³);

and
$R^4$ is hydrogen or alkyl.

In certain embodiments, the invention relates to any of the aforementioned compounds and attendant definitions, provided the compound is not

[structure: 2,4-difluorophenyl imino thiazoline with N-N=CH-2,4-dihydroxyphenyl and 2-furyl substituent].

In certain embodiments, the invention relates to any of the aforementioned compounds and attendant definitions, wherein

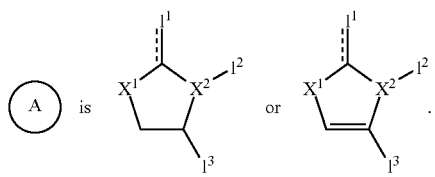
In certain embodiments, the invention relates to any of the aforementioned compounds and attendant definitions, wherein
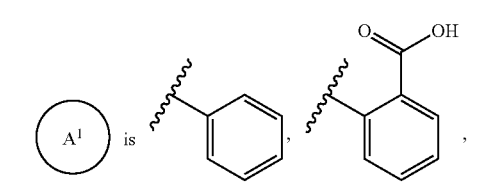
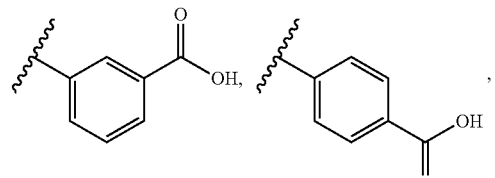
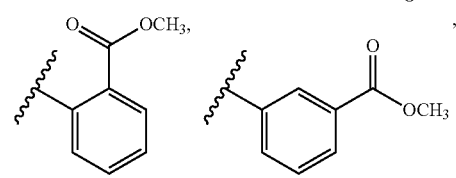
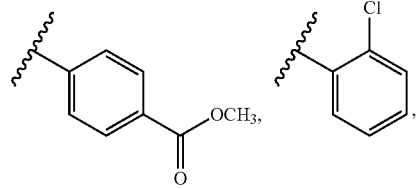
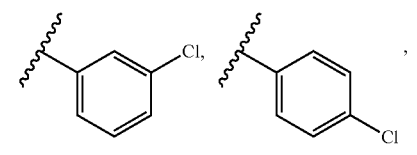
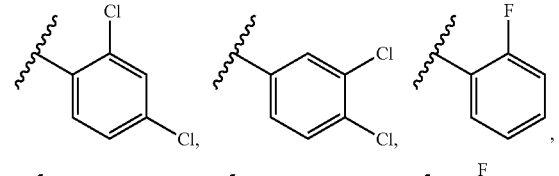
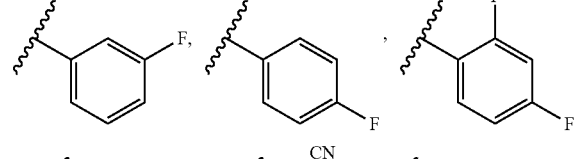
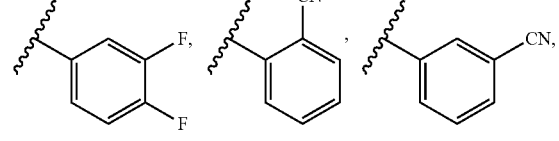
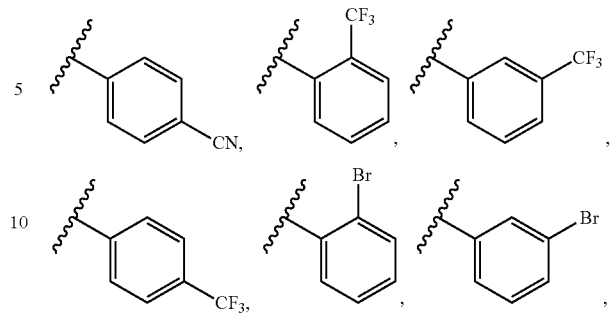
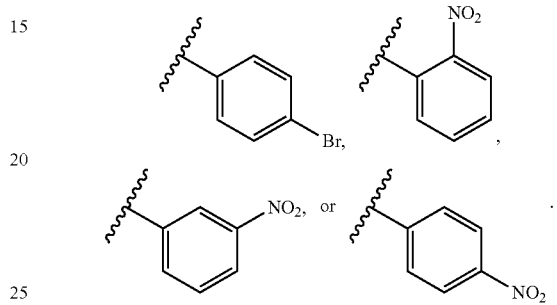
In certain embodiments, the invention relates to any of the aforementioned compounds and attendant definitions, wherein
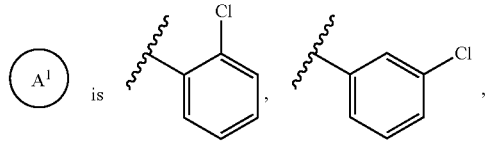
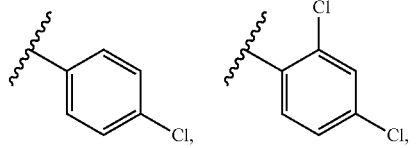
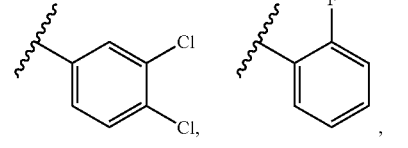
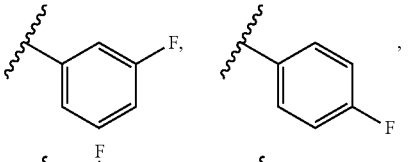
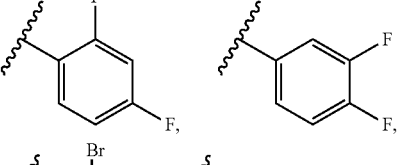
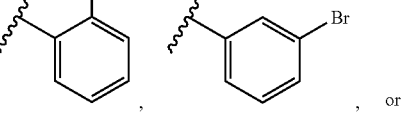

In certain embodiments, the invention relates to any of the aforementioned compounds and attendant definitions, wherein

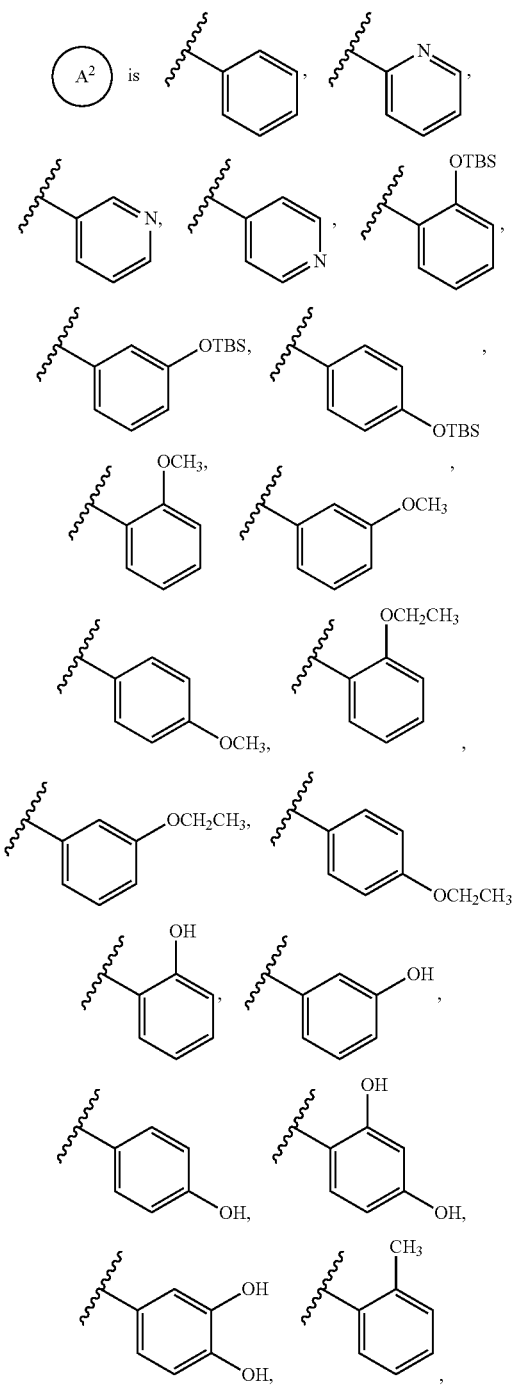

A² is [shown structures including phenyl, 2-pyridyl, 3-pyridyl, 4-pyridyl, 2-OTBS-phenyl, 3-OTBS-phenyl, 4-OTBS-phenyl, 2-OCH₃-phenyl, 3-OCH₃-phenyl, 4-OCH₃-phenyl, 2-OCH₂CH₃-phenyl, 3-OCH₂CH₃-phenyl, 4-OCH₂CH₃-phenyl, 2-OH-phenyl, 3-OH-phenyl, 4-OH-phenyl, 2,4-diOH-phenyl, 3,4-diOH-phenyl, 2-CH₃-phenyl, 4-Br-phenyl,

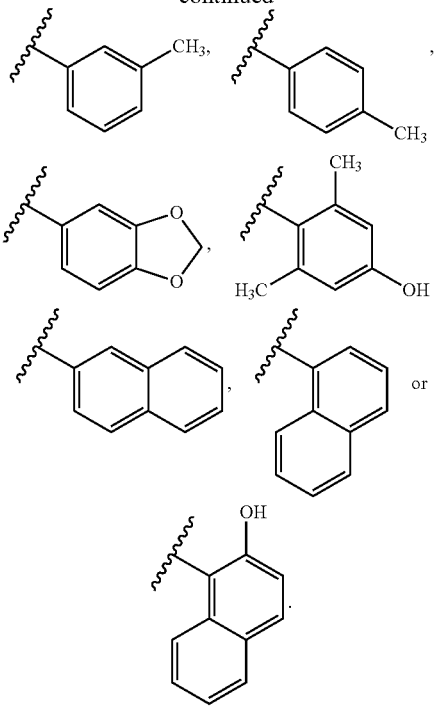

3-CH₃-phenyl, 4-CH₃-phenyl, benzo[1,3]dioxol-5-yl, 3,5-dimethyl-4-OH-phenyl, 2-naphthyl, 1-naphthyl, or 2-hydroxy-1-naphthyl].

In certain embodiments, the invention relates to any of the aforementioned compounds and attendant definitions, wherein

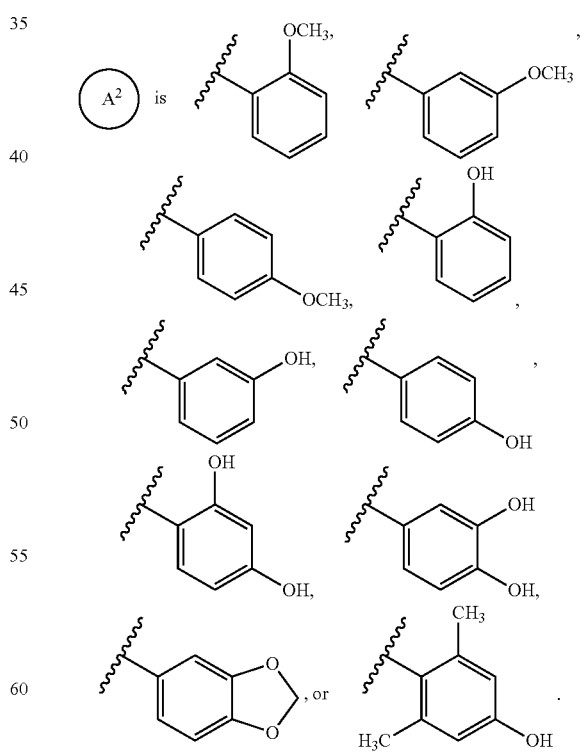

A² is [shown structures including 2-OCH₃-phenyl, 3-OCH₃-phenyl, 4-OCH₃-phenyl, 2-OH-phenyl, 3-OH-phenyl, 4-OH-phenyl, 2,4-diOH-phenyl, 3,4-diOH-phenyl, benzo[1,3]dioxol-5-yl, or 3,5-dimethyl-4-OH-phenyl].

In certain embodiments, the invention relates to any of the aforementioned compounds and attendant definitions, wherein

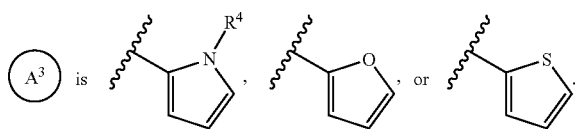

In certain embodiments, the invention relates to any of the aforementioned compounds and attendant definitions, wherein

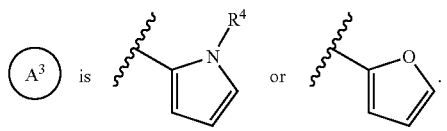

In certain embodiments, the invention relates to any of the aforementioned compounds and attendant definitions, wherein $L^1$ is

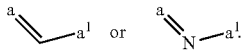

In certain embodiments, the invention relates to any of the aforementioned compounds and attendant definitions, wherein $L^1$ is

In certain embodiments, the invention relates to any of the aforementioned compounds and attendant definitions, wherein $L^2$ is

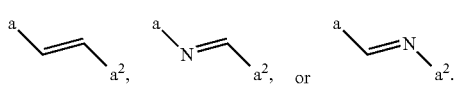

In certain embodiments, the invention relates to any of the aforementioned compounds and attendant definitions, wherein $L^2$ is

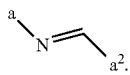

In certain embodiments, the invention relates to any of the aforementioned compounds and attendant definitions, wherein $L^3$ is a bond.

In certain embodiments, the invention relates to any of the aforementioned compounds and attendant definitions, wherein $X^1$ is O or S. In certain embodiments, the invention relates to any of the aforementioned compounds and attendant definitions, wherein $X^1$ is S.

In certain embodiments, the invention relates to any of the aforementioned compounds and attendant definitions, wherein $X^2$ is N.

In certain embodiments, the invention relates to any of the aforementioned compounds and attendant definitions, wherein $R^4$ is hydrogen. In certain embodiments, the invention relates to any of the aforementioned compounds and attendant definitions, wherein $R^4$ is alkyl. In certain embodiments, the invention relates to any of the aforementioned compounds and attendant definitions, wherein $R^4$ is methyl.

Another aspect of the invention relates to a compound represented by formula V:

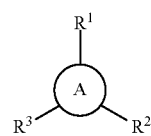

or a pharmaceutically acceptable salt, solvate, hydrate, prodrug, chemically-protected form, enantiomer or stereoisomer thereof; wherein, independently for each occurrence,

is a five-membered heteroaryl triradical;

$R^1$ is

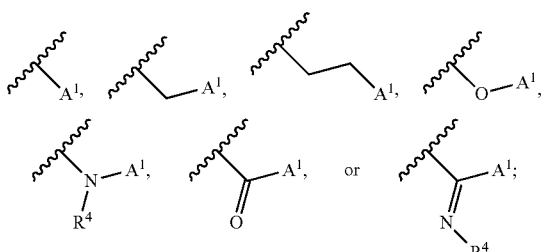

$R^2$ is

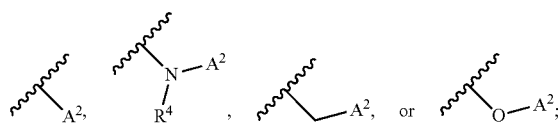

$R^3$ is halo, cyano, haloalkyl, hydroxy, alkyloxy, haloalkyloxy, alkylcarbonyloxy, haloalkylcarbonyloxy, carboxy, alkyloxycarbonyl, haloalkyloxycarbonyl, amino, nitro, or amido;

$A^1$ is a substituted or unsubstituted six-membered aryl or heteroaryl ring;

$A^2$ is a substituted or unsubstituted five-membered heteroaryl ring; and $R^4$ is hydrogen, alkyl, haloalkyl, aryl, heteroaryl, aralkyl, heteroaralkyl, alkylcarbonyl, haloalkyl, arylcarbonyl, heteroarylcarbonyl, aralkylcarbonyl or heteroaralkylcarbonyl.

In certain embodiments, the invention relates to any of the aforementioned compounds and attendant definitions, provided the compound is not

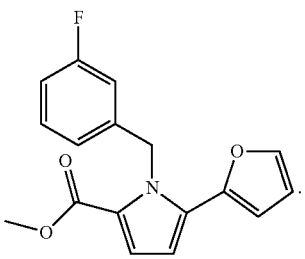 [SMILES: COC(=O)c1ccc(-c2ccco2)n1Cc1cccc(F)c1]

In certain embodiments, the invention relates to any of the aforementioned compounds and attendant definitions, wherein

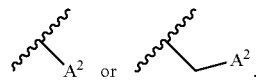

is pyrrole triradical, thiophene triradical, furan triradical, imidazole triradical, oxazole triradical, or thiazole triradical. In certain embodiments, the invention relates to any of the aforementioned compounds and attendant definitions, wherein

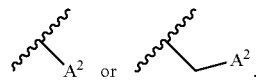

is pyrrole triradical, thiophene triradical, or furan triradical. In certain embodiments, the invention relates to any of the aforementioned compounds and attendant definitions, wherein

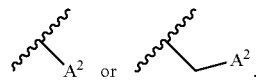

is pyrrole triradical.

In certain embodiments, the invention relates to any of the aforementioned compounds and attendant definitions, wherein $R^1$ is

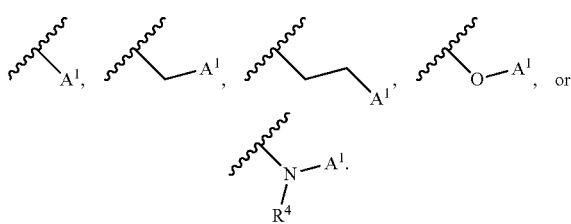

In certain embodiments, the invention relates to any of the aforementioned compounds and attendant definitions, wherein $R^1$ is

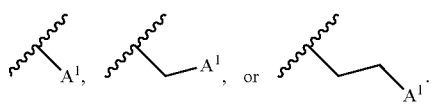

In certain embodiments, the invention relates to any of the aforementioned compounds and attendant definitions, wherein $R^2$ is

[figures showing two structures with $A^2$]

In certain embodiments, the invention relates to any of the aforementioned compounds and attendant definitions, wherein $R^2$ is

In certain embodiments, the invention relates to any of the aforementioned compounds and attendant definitions, wherein $R^3$ is halo, cyano, alkylcarbonyloxy, haloalkylcarbonyloxy, carboxy, alkyloxycarbonyl, haloalkyloxycarbonyl, nitro, or amido. In certain embodiments, the invention relates to any of the aforementioned compounds and attendant definitions, wherein $R^3$ is alkylcarbonyloxy, carboxy, alkyloxycarbonyl, or amido.

In certain embodiments, the invention relates to any of the aforementioned compounds and attendant definitions, wherein $A^1$ is substituted or unsubstituted phenyl or pyridyl. In certain embodiments, the invention relates to any of the aforementioned compounds and attendant definitions, wherein $A^1$ is substituted phenyl or substituted pyridyl. In certain embodiments, the invention relates to any of the aforementioned compounds and attendant definitions, wherein $A^1$ is 2-substituted phenyl, 3-substituted phenyl, or 4-substituted phenyl. In certain embodiments, the invention relates to any of the aforementioned compounds and attendant definitions, wherein $A^1$ is 3-halophenyl. In certain embodiments, the invention relates to any of the aforementioned compounds and attendant definitions, wherein $A^1$ is 3-fluorophenyl.

In certain embodiments, the invention relates to any of the aforementioned compounds and attendant definitions, wherein $A^2$ is substituted or unsubstituted pyrrole, thiophene, furan, imidazole, oxazole, or thiazole. In certain embodiments, the invention relates to any of the aforementioned compounds and attendant definitions, wherein $A^3$ is unsubstituted pyrrole, thiophene, furan, imidazole, oxazole, or thiazole. In certain embodiments, the invention relates to any of the aforementioned compounds and attendant definitions, wherein $A^3$ is substituted or unsubstituted pyrrole, thiophene, or furan. In certain embodiments, the invention relates to any of the aforementioned compounds and attendant definitions, wherein $A^3$ is substituted or unsubstituted furan.

In certain embodiments, the invention relates to any of the aforementioned compounds and attendant definitions, wherein $R^4$ is hydrogen, alkyl, aralkyl, alkylcarbonyl or aralkylcarbonyl. In certain embodiments, the invention relates to any of the aforementioned compounds and attendant definitions, wherein $R^4$ is hydrogen. In certain embodiments, the invention relates to any of the aforementioned compounds and attendant definitions, wherein $R^4$ is alkyl. In certain embodiments, the invention relates to any of the aforementioned compounds and attendant definitions, wherein $R^4$ is methyl.

Another aspect of the invention relates to a subset of compounds of formula V which are represented by formula VI:

VI
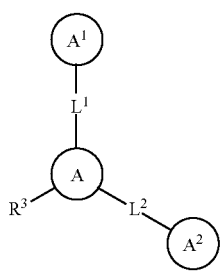
or a pharmaceutically acceptable salt, solvate, hydrate, prodrug, chemically-protected form, enantiomer or stereoisomer thereof; wherein, independently for each occurrence,
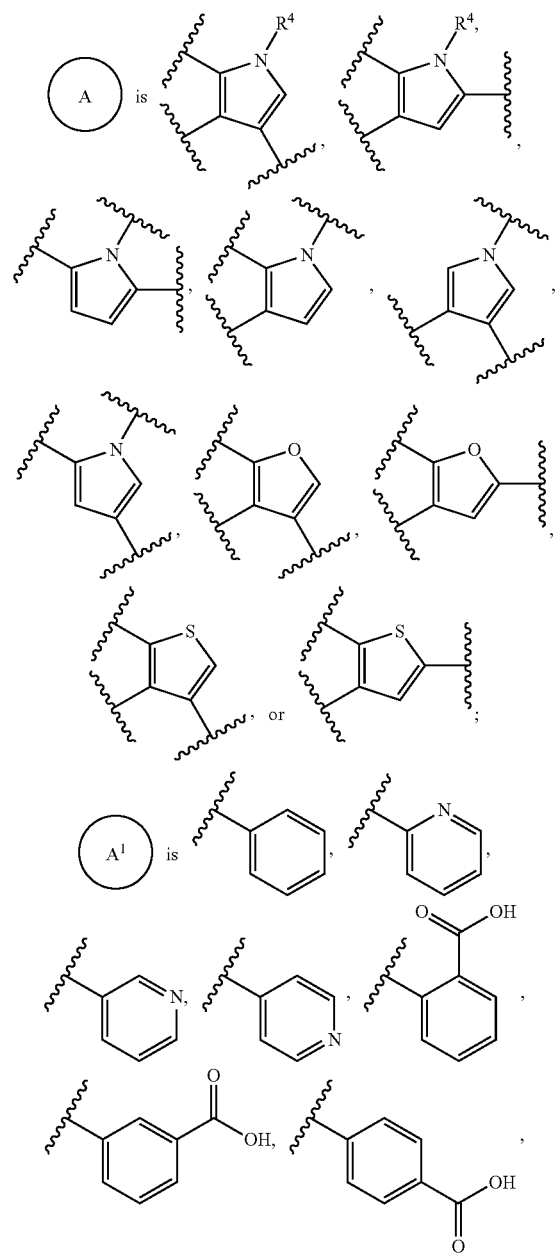
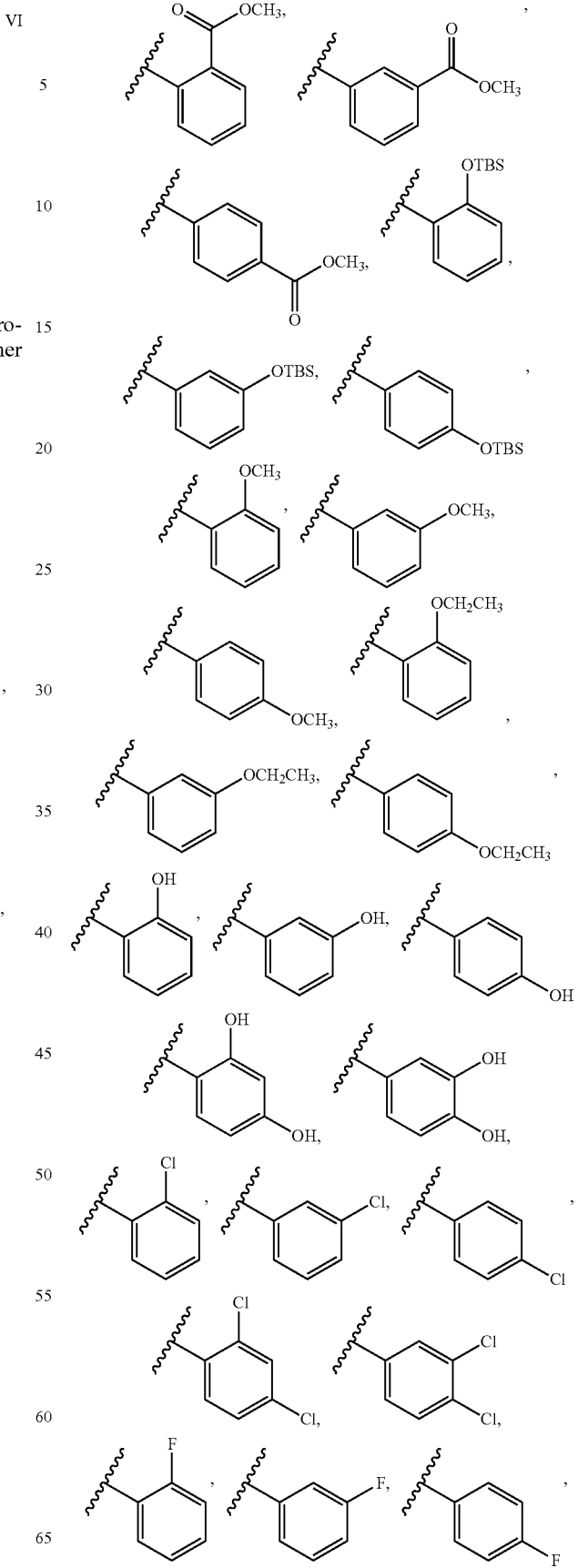

L¹ is a bond, $$\overset{a}{\diagup}a^1, \quad \overset{a}{\diagup}O\diagdown a^1, \quad \text{or} \quad \overset{a}{\diagup}\underset{R^4}{N}\diagdown a^1;$$

L² is a bond or $$\overset{a}{\diagup}a^2;$$

R³ is —Cl, —F, —Br, —CN, —C(O)R⁴, —C(O)—OR⁴, —C(O)NR⁴, or —NO₂;

a is a bond to (A);

a¹ is a bond to (A¹);

a² is a bond to (A²);

and

R⁴ is hydrogen or alkyl.

In certain embodiments, the invention relates to any of the aforementioned compounds and attendant definitions, provided the compound is not

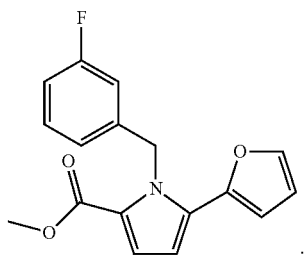 [SMILES: COC(=O)c1ccc(-c2ccco2)n1Cc1cccc(F)c1]

In certain embodiments, the invention relates to any of the aforementioned compounds and attendant definitions, wherein

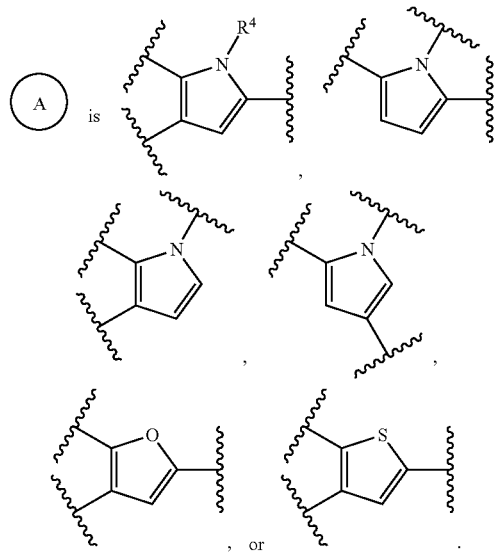

In certain embodiments, the invention relates to any of the aforementioned compounds and attendant definitions, wherein

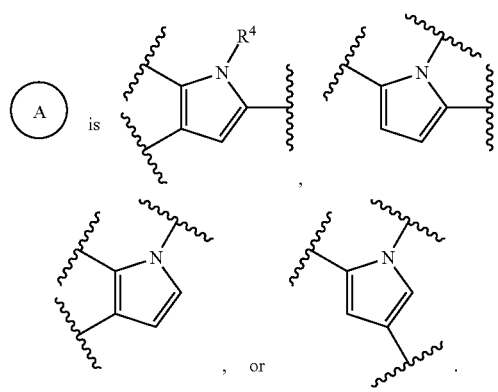

In certain embodiments, the invention relates to any of the aforementioned compounds and attendant definitions, wherein

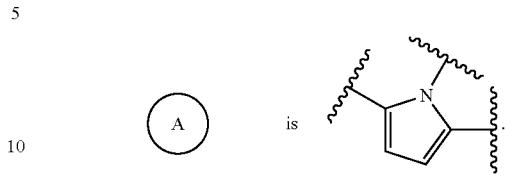

In certain embodiments, the invention relates to any of the aforementioned compounds and attendant definitions, wherein

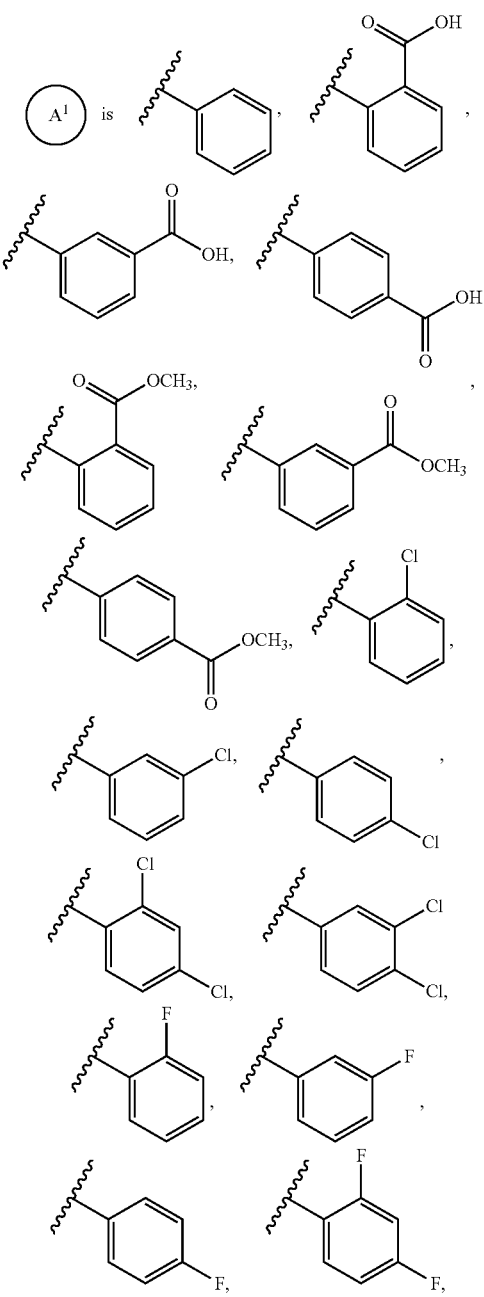

-continued

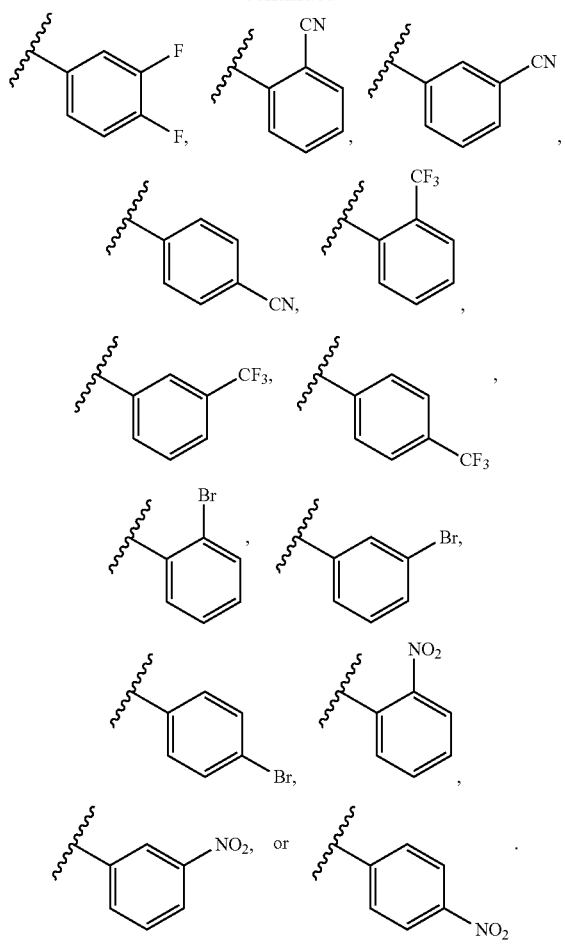

In certain embodiments, the invention relates to any of the aforementioned compounds and attendant definitions, wherein

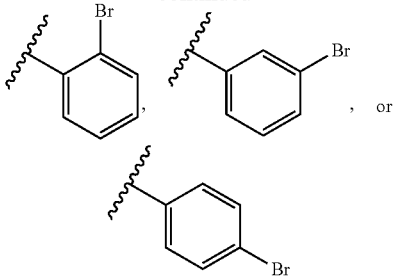

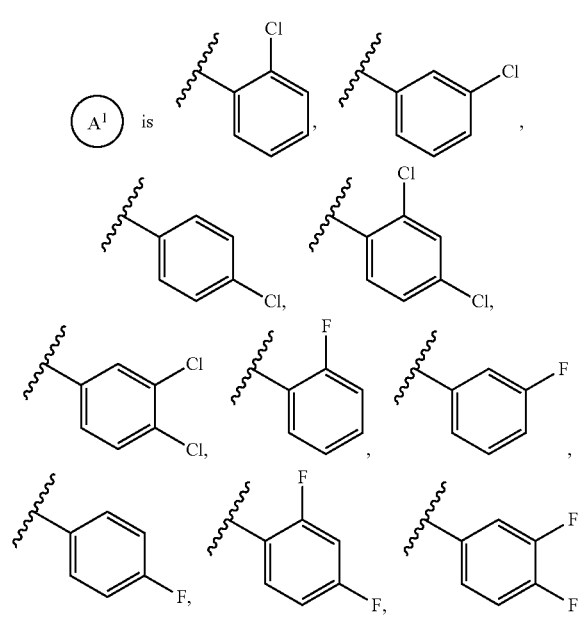

In certain embodiments, the invention relates to any of the aforementioned compounds and attendant definitions, wherein

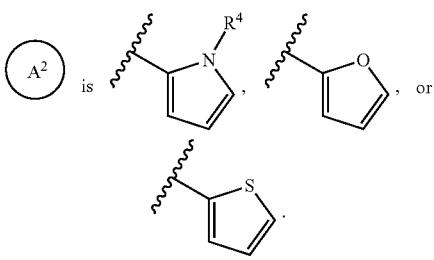

In certain embodiments, the invention relates to any of the aforementioned compounds and attendant definitions, wherein $L^1$ is a bond,

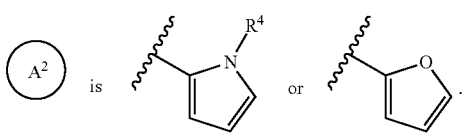

In certain embodiments, the invention relates to any of the aforementioned compounds and attendant definitions, wherein $L^1$ is a bond or

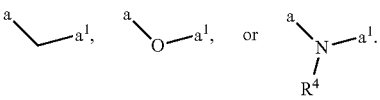

In certain embodiments, the invention relates to any of the aforementioned compounds and attendant definitions, wherein $L^1$ is

In certain embodiments, the invention relates to any of the aforementioned compounds and attendant definitions, wherein $L^2$ is a bond.

In certain embodiments, the invention relates to any of the aforementioned compounds and attendant definitions, wherein $R^3$ is —C(O)$R^4$, —C(O)—O$R^4$, —C(O)N$R^4$, or —NO$_2$. In certain embodiments, the invention relates to any of the aforementioned compounds and attendant definitions, wherein $R^3$ is —C(O)—O$R^4$ or —C(O)N$R^4$.

In certain embodiments, the invention relates to any of the aforementioned compounds and attendant definitions, wherein $R^4$ is hydrogen. In certain embodiments, the invention relates to any of the aforementioned compounds and attendant definitions, wherein $R^4$ is alkyl. In certain embodiments, the invention relates to any of the aforementioned compounds and attendant definitions, wherein $R^4$ is methyl.

Many of the compounds of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Certain compounds of the invention and their salts may exist in more than one crystal form and the present invention includes each crystal form and mixtures thereof.

Certain compounds of the invention and their salts may also exist in the form of solvates, for example hydrates, and the present invention includes each solvate and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of the invention and mixtures thereof.

Certain compounds of the invention may exist in different tautomeric forms or as different geometric isomers, and the present invention includes each tautomer and/or geometric isomer of compounds of the invention and mixtures thereof.

Certain compounds of the invention may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of the invention and mixtures thereof.

Certain compounds of the invention may exist in zwitterionic form and the present invention includes each zwitterionic form of compounds of the invention and mixtures thereof.

The present invention also includes pro-drugs. As used herein the term "pro-drug" refers to an agent that is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —C(O)$_2$H or a moiety that contains a carboxylic acid) wherein the free hydrogen is replaced by ($C_1$-$C_4$)alkyl, ($C_2$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino($C_2$-$C_3$) alkyl.

Other exemplary pro-drugs release an alcohol or amine of a compound of the invention wherein the free hydrogen of a hydroxyl or amine substituent is replaced by ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyl-oxymethyl, N—($C_1$-$C_6$)alkoxycarbonylamino-methyl, succinoyl, ($C_1$-$C_6$)alkanoyl, α-amino($C_1$-$C_4$)alkanoyl, arylacyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O($C_1$-$C_6$)alkyl)$_2$ or glycosyl (the radical resulting from detachment of the hydroxyl of the hemiacetal of a carbohydrate).

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Protected forms of the inventive compounds are included within the scope of this invention.

The term "chemically protected form," as used herein, pertains to a compound in which one or more reactive functional groups are protected from undesirable chemical reactions, that is, are in the form of a protected or protecting group (also known as a masked or masking group). It may be convenient or desirable to prepare, purify, and/or handle the active compound in a chemically protected form.

By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(═O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(═O)$CH_3$, —OAc).

For example, an aldehyde or ketone group may be protected as an acetal or ketal, respectively, in which the carbonyl group (C(═O)) is converted to a diether (C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRC(═O)R) or a urethane (—NRC(═O)OR), for example, as: a methyl amide (—NHC(═O)$CH_3$); a benzyloxy amide (—NHC(═O)OCH$_2$C$_6$H$_5$NHCbz); as a t-butoxy amide (—NHC═(═O)OC(CH$_3$)$_3$, —NHBoc); a 2-biphenyl-2-propoxy amide (—NHC(═O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; or an acetamidomethyl ether (—SCH$_2$NHC(═O)CH$_3$).

The compounds described herein are isolated molecules. An isolated molecule is a molecule that is substantially pure and is free of other substances with which it is ordinarily found in nature or in vivo systems to an extent practical and appropriate for its intended use. In particular, the molecular species are sufficiently pure and are sufficiently free from other biological constituents of host cells so as to be useful in, for example, producing pharmaceutical preparations or sequencing if the molecular species is a nucleic acid, peptide, or polysaccharide. Because an isolated molecular species of the invention may be admixed with a pharmaceutically-acceptable carrier in a pharmaceutical preparation or be mixed with some of the components with which it is associated in nature, the molecular species may comprise only a small percentage by weight of the preparation. The molecular species is nonetheless substantially pure in that it has been substantially separated from the substances with which it may be associated in living systems.

Exemplary Methods

The invention relates in some aspects to methods of treating viral infection in a subject, such as Ebola and Lassa fever, comprising administering an effective amount of a compound of formula I, II, III, IV, V, or VI, or pharmaceutically acceptable salt, solvate, hydrate, prodrug, chemically-protected form, enantiomer or stereoisomer thereof, to the subject in need thereof The invention relates in some aspects to methods of treating both Ebola and Lassa fever, comprising administering an effective amount of a compound of formula I, II, III, IV, V, or VI, or pharmaceutically acceptable salt, solvate, hydrate, prodrug, chemically-protected form, enantiomer or stereoisomer thereof, to the subject in need thereof.

The invention relates in some aspects to methods of simultaneously treating both Ebola and Lassa fever, comprising administering an effective amount of a compound of formula I, II, III, IV, V, or VI, or pharmaceutically acceptable salt, solvate, hydrate, prodrug, chemically-protected form, enantiomer or stereoisomer thereof, to the subject in need thereof The invention relates in some aspects to methods of inhibiting Ebola and Lassa fever viruses in a cell, comprising administering an effective amount of a compound of formula I, II, III, IV, V, or VI, or pharmaceutically acceptable salt, solvate, hydrate, prodrug, chemically-protected form, enantiomer or stereoisomer thereof, to the subject in need thereof Although Applicant is not bound by a mechanism, it is believed that the compounds of the invention are useful for treating Ebola infection by interfering with the activation of the cleaved GP1 glycoprotein subunit to trigger membrane fusion and cell entry. As shown in FIG. 1, one hypothesis is that the initial step in infection is proposed to be cleavage of GP1 by a cathepsin such as (CatB and/or CatL) to remove C-terminal sequences and generate an N-terminal GP1-18K-like species. It is proposed that the second step, removal of the N-terminal GP1-18K-like species, is inhibited by the compounds of the invention.

Again, not intending to be bound by a mechanism, it is also hypothesized that the compounds of the invention block calcium or other ion channels, such as sodium or potassium, in the host, whose activities are necessary for Ebola and Lassa fever virus particles to be transported from the cell surface to the specific vesicular compartment in the cell with GP activation, virus fusion and entry occurs. This hypothesis is based in part on some similarities between known compounds and existing drugs, including some anti-histamines, tamoxifen, and the anti-cardiac arrhythmic drugs amiodarone, diltiazen and amlodipne. Shared properties of the existing drugs are: inhibiting calcium channels, and possessing weak anti-EboV activity.

Several viruses produce a syndrome referred to as hemorrhagic fever following infection of humans. Although the viruses are not structurally similar, they produce this syndrome in humans, which is characterized by an exaggerated immune response. Often the viruses that produce this type of systemic inflammatory response resulting in hemorrhagic fever have transferred from a different species to humans. Examples of viruses that fall into this category include Ebola, Lassa fever, Marburg, Nipah, Hendra, and avian-derived influenza. The methods of the invention are particularly useful for treating Ebola and Lassa fever viruses.

The methods of the invention are useful for treating a subject in need thereof. A subject in need thereof is a subject having or at risk of having an enveloped virus infection. In its broadest sense, the terms "treatment" or "to treat" refer to both therapeutic and prophylactic treatments. If the subject in need of treatment is experiencing a condition (i.e., has or is having a particular condition), then "treating the condition" refers to ameliorating, reducing or eliminating one or more symptoms arising from the condition. If the subject in need of treatment is one who is at risk of having a condition, then treating the subject refers to reducing the risk of the subject having the condition or, in other words, decreasing the likelihood that the subject will develop an infectious disease to the virus, as well as to a treatment after the subject has been infected in order to fight the infectious disease, e.g., reduce or eliminate it altogether or prevent it from becoming worse.

Thus the invention encompasses the use of the inhibitors described herein alone or in combination with other therapeutics for the treatment of a subject having or at risk of having a viral infection, e.g., an enveloped viral infection. A "subject having an enveloped viral infection" is a subject that has had contact with a virus. Thus the virus has invaded the body of the subject. The word "invade" as used herein refers to contact by the virus with an external surface of the subject, e.g., skin or mucosal membranes and/or refers to the penetration of the external surface of the subject by the virus. A subject at risk of having an enveloped virus infection is one that has been exposed to or may become exposed to an enveloped virus or a geographical area in which an enveloped viral infection has been reported. Further risks include close contact with a human or non-human primate or their tissues infected with the virus. Such persons include laboratory or quarantine facility workers who handle non-human primates that have been associated with the disease. In addition, hospital staff and family members who care for patients with the disease are at risk if they do not use proper barrier nursing techniques.

As used herein, a subject includes humans and non-human animals such as non-human primates, dogs, cats, sheep, goats, cows, pigs, horses and rodents.

The invention provides methods and compositions to treat conditions which would benefit from, and which thus can be treated by, an inhibition of the activation of N-terminal GP1-18K-like species, such as infection by enveloped viruses.

The compositions are delivered in effective amounts. The term "effective amount" refers to the amount necessary or sufficient to realize a desired biologic effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. In addition, based on testing, toxicity of the inhibitor is expected to be low. The effective amount for any particular application can vary depending on such factors as the disease or condition being treated, the particular inhibitor being administered, the size of the subject, or the severity of the disease or condition. One of ordinary skill in the art can empirically determine the effective amount of a particular inhibitor and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

For any compound described herein, the therapeutically effective amount can be initially determined from preliminary in vitro studies and/or animal models. A therapeutically effective dose can also be determined from human data for inhibitors which have been tested in humans and for compounds which are known to exhibit similar pharmacological activities, such as other related active agents. The applied dose can be adjusted based on the relative bioavailability and potency of the administered compound. Adjusting the dose to achieve maximal efficacy based on the methods described above and other methods well-known in the art, is well within the capabilities of the ordinarily skilled artisan.

In certain embodiments, the methods of the invention are useful for treating infection with enveloped viruses. Viruses are small infectious agents which contain a nucleic acid core and a protein coat, but are not independently living organisms. A virus cannot multiply in the absence of a living cell within which it can replicate. Viruses enter specific living cells either by transfer across a membrane or direct injection and multiply, causing disease. The multiplied virus can then be released and infect additional cells. Some viruses are DNA-containing viruses and others are RNA-containing viruses. The genomic size, composition and organization of viruses show tremendous diversity.

As used herein, an "enveloped" virus is an animal virus which possesses a membrane or 'envelope', which is a lipid bilayer containing viral proteins. The envelope proteins of a virus play a pivotal role in its lifecycle. They participate in the assembly of the infectious particle and also play a crucial role in virus entry by binding to a receptor present on the host cell and inducing fusion between the viral envelope and a membrane of the host cell. Enveloped viruses can be either spherical or filamentous (rod-shaped) and include but are not limited to filoviruses, such as Ebola virus or Marburg virus, Lassa virus, Arboroviruses such as Togaviruses, flaviviruses (such as hepatitis-C virus), bunyaviruses, and Arenaviruses, Orthomyxoviridae, Paramyxoviridae, poxvirus, herpesvirus, hepadnavirus, Rhabdovirus, Bornavirus, and Arterivirus.

In some embodiments, the invention provides for methods of treating infection by Ebola virus. Four species of Ebola virus have been identified: Cote d'Ivoire (CI), Sudan (S), Zaire (Z), and Reston (R). The Reston subtype is the only known filovirus that is not known to cause fatal disease in humans; however, it can be fatal in monkeys. In some embodiments, the compounds of the invention can selectively inhibit Ebola infection.

Infection by Ebola virus leads to Ebola Hemorrhagic Fever (EHF), the clinical manifestations of which are severe. The incubation period varies between four and sixteen days. The initial symptoms are generally a severe frontal and temporal headache, generalized aches and pains, malaise, and by the second day the victim will often have a fever. Later symptoms include watery diarrhea, abdominal pain, nausea, vomiting, a dry sore throat, and anorexia. By day seven of the symptoms, the patient will often have a maculopapular (small slightly raised spots) rash. At the same time the person may develop thrombocytopenia and hemorrhagic manifestations, particularly in the gastrointestinal tract, and the lungs, but it can occur from any orifice, mucous membrane or skin site. Ebola causes lesions in almost every organ, although the liver and spleen are the most noticeably affected. Both are darkened and enlarged with signs of necrosis. The cause of death (>75% in most outbreaks) is normally shock, associated with fluid and blood loss into the tissues. The hemorrhagic and connective tissue complications of the disease are not well understood, but may be related to onset of disseminated intravascular coagulation.

As used herein, the term "Marburg virus" refers to the filovirus that causes Marburg hemorrhagic fever. Marburg hemorrhagic fever is a rare, severe type of hemorrhagic fever which affects both humans and non-human primates. The case-fatality rate for Marburg hemorrhagic fever is 70% in recent Angola outbreak. After an incubation period of 5-10 days, the onset of the disease is sudden and is marked by fever, chills, headache, and myalgia. Around the fifth day after the onset of symptoms, a maculopapular rash, most prominent on the trunk (chest, back, stomach), may occur. Nausea, vomiting, chest pain, a sore throat, abdominal pain, and diarrhea then may appear. Symptoms become increasingly severe and may include jaundice, inflammation of the pancreas, severe weight loss, delirium, shock, liver failure, massive hemorrhaging, and multi-organ dysfunction.

The family Orthomyxoviridae includes, without limitation, influenza A virus, influenza B virus, influenza C virus, Thogotovirus, Dhori virus, and infectious salmon anemia virus.

Influenza type A viruses are divided into subtypes based on two proteins on the surface of the virus. These proteins are called hemagglutinin (HA) and neuraminidase (NA). There are 15 different HA subtypes and 9 different NA subtypes. Subtypes of influenza A virus are named according to their HA and NA surface proteins, and many different combinations of HA and NA proteins are possible. For example, an "H7N2 virus" designates an influenza A subtype that has an HA 7 protein and an NA 2 protein. Similarly an "H5N1" virus has an HA 5 protein and an NA 1 protein. Only some influenza A subtypes (i.e., H1N1, H2N2, and H3N2) are currently in general circulation among people. Other subtypes such as H5 N1 are found most commonly in other animal species and in a small number of humans, where it is highly pathogenic. For example, H7N7 and H3N8 viruses cause illness in horses. Humans can be infected with influenza types A, B, and C. However, the only subtypes of influenza A virus that normally infect people are influenza A subtypes H1N1, H2N2, and H3N2 and recently, H5N1.

The family Paramyxoviridae includes, without limitation, human parainfluenza virus, human respiratory syncytial virus (RSV), Sendai virus, Newcastle disease virus, mumps virus, rubeola (measles) virus, Hendra virus, Nipah virus, avian pneumovirus, and canine distemper virus. The family Filoviridae includes, without limitation, Marburg virus and Ebola virus. The family Rhabdoviridae includes, without limitation, rabies virus, vesicular stomatitis virus (VSV), Mokola virus, Duvenhage virus, European bat virus, salmon infectious hematopoietic necrosis virus, viral hemorrhagic septicaemia virus, spring viremia of carp virus, and snakehead rhabdovirus. The family Bornaviridae includes, without limitation, Borna disease virus. The family Bunyaviridae includes, without limitation, Bunyamwera virus, Hantaan virus, Crimean Congo virus, California encephalitis virus, Rift Valley fever virus, and sandfly fever virus. The family Arenaviridae includes, without limitation, Old World Arenaviruses, such as Lassa virus (Lassa fever), Ippy virus, Lymphocytic choriomeningitis virus (LCMV), Mobala virus, and Mopeia virus and New World Arenaviruses, such as Junin virus (Argentine hemorrhagic fever), Sabia (Brazilian hemorrhagic fever), Amapari virus, Flexal virus, Guanarito virus (Venezuela hemorrhagic fever), Machupo virus (Bolivian hemorrhagic fever), Latino virus, Boliveros virus, Parana virus, Pichinde virus, Pirital virus, Tacaribe virus, Tamiami virus, and Whitewater Arroyo virus. The Arenaviridae associated with specific diseases include Lymphocytic choriomeningitis virus (meningitis), Lassa virus (hemorrhagic fever), Junin Virus (Argentine hemorrhagic fever), Machupo Virus (Bolivian hemorrhagic fever), Sabia virus (Brazilian hemorrhagic fever), and Guanarito (Venezuelan Hemorrhagic fever).

The arboviruses are a large group (more than 400) of enveloped RNA viruses that are transmitted primarily (but not exclusively) by arthropod vectors (mosquitoes, sand-flies, fleas, ticks, lice, etc.). More recently, the designated Arborviruses have been split into four virus families, including the togaviruses, flaviviruses, arenaviruses and bunyaviruses.

As used herein, the term "togavirus" refers to members of the family Togaviridae, which includes the genuses Alphavirus (e.g. Venezuela equine encephalitis virus, Sindbis virus, which causes a self-limiting febrile viral disease characterized by sudden onset of fever, rash, arthralgia or arthritis, lassitude, headache and myalgia) and Rubivirus (e.g. Rubella virus, which causes Rubella in vertebrates).

Rubella virus infections in adults are frequently sub-clinical. A characteristic pink, continuous maculopapular rash appears in 95% of adolescent patients 14-25 days after infection, and the patient is infectious for most of this time. After early viremia, rubella virus multiplies in many organs, particularly lymph nodes (lymphadenopathy), including the placenta, but symptoms in adults are rare. In children Rubella virus causes a mild febrile illness. The virus crosses placenta and multiplies in the fetus. Up to 85% of infants infected in the first trimester of pregnancy get congenital rubella syndrome (CRS), characterized by low birth weight, deafness, CNS involvement, and possibly abortion, with symptoms worse the earlier in pregnancy they occur.

Flaviviridae is a member of the family of (+)-sense RNA enveloped viruses. Flaviviridae includes flavivirus, Pestivirus, and Hepacivirus. Flavivirus genus including yellow fever virus, dengue fever virus, and Japanese encephalitis (JE) virus. The Pestivirus genus includes the three serotypes of bovine viral diarrhea, but no known human pathogens. Genus Hepacivirus consists of hepatitis C virus and hepatitis C-like viruses.

A yellow fever virus infection is characterized by an incubation period of 3 to 6 days, during which 5% to 50% of infected people develop disease. Yellow fever begins with a nonspecific 1- to 3-day febrile illness, followed by a brief remission, and then by a life-threatening toxic syndrome accompanied by epistaxis, other hemorrhagic phenomena, jaundice, and disseminated intravascular coagulation. Mortality rates for yellow fever are approximately 20%.

There are four serotypes of dengue fever virus, all transmitted by mosquitos. Dengue fever virus infection may be asymptomatic or may result in dengue fever. This is generally a self-limiting febrile illness which occurs after a 4-8 day incubation period. It has symptoms such as fever, aches and arthralgia (pain in the joints) which can progress to arthritis (inflammation of the joints), myositis (inflammation of muscle tissue) and a discrete macular or maculopapular rash. In this situation clinical differentiation from other viral illnesses may not be possible, recovery is rapid, and need for supportive treatment is minimal. Dengue haemorrhagic fever (DHF) is a potentially deadly complication. Dengue hemorrhagic fever commences with high fever and many of the symptoms of dengue fever, but with extreme lethargy and drowsiness. The patient has increased vascular permeability and abnormal homeostasis that can lead to hypovolemia and hypotension, and in severe cases, result in hypovolemic shock often complicated by severe internal bleeding.

The Japanese encephalitis antigenic complex includes Alfuy, Japanese encephalitis, Kokobera, Koutango, Kunjin, Murray Valley encephalitis, St. Louis encephalitis, Stratford, Usutu, and West Nile viruses. These viruses are transmissible by mosquitoes and many of them can cause febrile, sometimes fatal, illnesses in humans. West Nile virus is the most widespread of the flaviviruses, with geographic distribution including Africa and Eurasia. West Nile virus RNA has been detected in overwintering mosquitoes in New York City & the geographic range of the virus is increasing in the USA.

The genus Pestivirus has been divided into bovine viral diarrhea virus (BVDV), classical swine fever virus (CSFV), and border disease virus (BDV). Infection with BVDV results in a variety of diseases ranging from subclinical to highly fatal. Many BVDV viruses cause only clinically mild disease in nonpregnant adult cattle. Prenatal infection can cause congenital malformations and/or fetal death.

The Hepacivirus genus includes the hepatitis C virus (HCV). The majority of cases of HCV infection give rise to an acute illness, where up to 85% of infections may develop into chronic hepatitis. Almost all patients develop a vigorous antibody and cell-mediated immune response which fails to clear the infection but may contribute towards liver damage.

Arenaviridae is a member of the family of (−) sense RNA viruses. As used herein, the term "Arenavirus" refers to members of the genus Arenavirus, a family of viruses whose members are generally associated with rodent-transmitted disease in humans, including Lymphocytic choriomeningitis virus (LCMV), Lassa virus, Junin virus, which causes Argentine hemorrhagic fever, Machupo virus, which causes Bolivian hemorrhagic fever, Guanarito virus, which causes Venezuelan hemorrhagic fever, and Sabia, which causes Brazilian hemorrhagic fever. LCMV causes which causes lymphocytic choriomeningitis, a mild disease that is occasionally severe with hemorrhaging. Infection by LCMV is rare in humans. Lassa virus causes Lassa fever in humans. Signs and symptoms of Lassa fever typically occur 1-3 weeks after the patient comes into contact with the virus. These include fever, retrosternal pain, sore throat, back pain, cough, abdominal pain, vomiting, diarrhea, conjunctivitis, facial swelling, proteinuria, and mucosal bleeding. Neurological problems have also been described, including hearing loss, tremors, and encephalitis.

Bunyaviridae is a family of (−)-sense RNA viruses. As used herein, "bunyavirus" refers to members of the Bunyaviridae family and includes the genuses Orthobunyavirus, Hantavirus, Phlebovirus, and Nairovirus.

Hantavirus infection is spread from rodents (reservoir) to man by aerosolized feces, not insect vector, causing hantavirus pulmonary syndrome (HPS). Patients with HPS typically present in with a relatively short febrile prodrome lasting 3-5 days. In addition to fever and myalgias, early symptoms include headache, chills, dizziness, non-productive cough, nausea, vomiting, and other gastrointestinal symptoms. Malaise, diarrhea, and lightheadedness are reported by approximately half of all patients, with less frequent reports of arthralgias, back pain, and abdominal pain. Patients may report shortness of breath, (respiratory rate usually 26-30 times per minute). Typical findings on initial presentation include fever, tachypnea and tachycardia. The physical examination is usually otherwise normal.

In man, the Phlebovirus Rift valley fever virus produces an acute, flu-like illness and is transmitted by mosquitoes from animal reservoirs (e.g. sheep) to man. Sand fly fever is transmitted to man by Phlebotomous flies (sand-flies) and causes an acute, febrile illness characterized by fever, malaise, eye pain, and headache.

Hendra and Nipah virus in the Henipavirus genus of the subfamily Paramyxovirinae are distinguished by fatal disease in both animal and human hosts. In particular, the high mortality and person-to-person transmission associated with the most recent Nipah virus outbreak.

In certain embodiments, the invention relates to a method of inhibiting endosomal membrane protein Niemann-Pick C1 (NPC1) in a cell, comprising contacting the cell with an effective amount of any one of the aforementioned compounds.

In certain embodiments, the invention relates to a method of treating or preventing a viral infection in a subject, comprising administering an effective amount of a compound that inhibits NPC1.

Not wishing to be bound by any particular theory, NPC1 is essential for infection; it binds to the virus glycoprotein (GP). In certain embodiments, the antiviral compounds interfere with GP binding to NPC1. Combined with the results of previous studies of GP structure and function, these findings support a model of EboV infection in which cleavage of the GP1 subunit by endosomal cathepsin proteases removes heavily glycosylated domains to expose the amino-terminal domain, which is a ligand for NPC1 and regulates membrane fusion by the GP2 subunit. Thus, NPC1 is essential for EboV entry and a target for antiviral therapy. The proposed mechanism is described in more detail in U.S. Provisional Patent Application Ser. No. 61/521,998, filed Aug. 10, 2011, hereby incorporated by reference in it is entirety.

Combination Therapy

The inhibitors of the invention can be combined with other therapeutic agents. The inhibitor and other therapeutic agent may be administered simultaneously or sequentially. When the other therapeutic agents are administered simultaneously they can be administered in the same or separate formulations, but are administered at the same time. The other therapeutic agents are administered sequentially with one another and with the inhibitors, when the administration of the other therapeutic agents and the inhibitors is temporally separated. The separation in time between the administration of these compounds may be a matter of minutes or it may be longer. Other therapeutic agents include but are not limited to anti-viral vaccines and anti-viral agents. In some instances the inhibitors are administered with multiple therapeutic agents, i.e., 2, 3, 4 or even more different anti-viral agents.

An anti-viral vaccine is a formulation composed of one or more viral antigens and one or more adjuvants. The viral antigens include proteins or fragments thereof as well as whole killed virus. Adjuvants are well known to those of skill in the art.

Antiviral agents are compounds which prevent infection of cells by viruses or replication of the virus within the cell. There are many fewer antiviral drugs than antibacterial drugs because viruses are more dependent on host cell factors than bacteria. There are several stages within the process of viral infection which can be blocked or inhibited by antiviral agents. These stages include, attachment of the virus to the host cell (immunoglobulin or binding peptides), membrane penetration inhibitors, e.g. T-20, uncoating of the virus (e.g. amantadine), synthesis or translation of viral mRNA (e.g. interferon), replication of viral RNA or DNA (e.g. nucleotide analogues), maturation of new virus proteins (e.g. protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, and resimiquimod.

The interferons are cytokines which are secreted by virus-infected cells as well as immune cells. The interferons function by binding to specific receptors on cells adjacent to the infected cells, causing the change in the cell which protects it from infection by the virus. α- and β-interferon also induce the expression of Class I and Class II MHC molecules on the surface of infected cells, resulting in increased antigen presentation for host immune cell recognition. α- and β-interferons are available as recombinant forms and have been used for the treatment of chronic hepatitis B and C infection. At the dosages which are effective for anti-viral therapy, interferons have severe side effects such as fever, malaise and weight loss.

Anti-viral agents which may be useful in combination with the inhibitors of the invention include but are not limited to immunoglobulins, amantadine, interferons, nucleotide analogues, and other protease inhibitors (other than the papain-like cysteine protease inhibitors—although combinations of papain-like cysteine protease inhibitors are also useful). Specific examples of anti-viral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Immunoglobulin therapy is used for the prevention of viral infection. Immunoglobulin therapy for viral infections is different than bacterial infections, because rather than being antigen-specific, the immunoglobulin therapy functions by binding to extracellular virions and preventing them from attaching to and entering cells which are susceptible to the viral infection. The therapy is useful for the prevention of viral infection for the period of time that the antibodies are present in the host. In general there are two types of immunoglobulin therapies, normal immunoglobulin therapy and hyper-immunoglobulin therapy. Normal immune globulin therapy utilizes a antibody product which is prepared from the serum of normal blood donors and pooled. This pooled product contains low titers of antibody to a wide range of human viruses, such as hepatitis A, parvovirus, enterovirus (especially in neonates). Hyper-immune globulin therapy utilizes antibodies which are prepared from the serum of individuals who have high titers of an antibody to a particular virus. Those antibodies are then used against a specific virus. Another type of immunoglobulin therapy is active immunization. This involves the administration of antibodies or antibody fragments to viral surface proteins.

Exemplary Pharmaceutical Compositions

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the inhibitor can be administered to a subject by any mode that delivers the inhibitor to the desired surface. Administering the pharmaceutical composition of the present invention may be accomplished by any means known to the skilled artisan. Preferred routes of administration include but are not limited to oral, intrathecal, intra-arterial, direct bronchial application, parenteral (e.g. intravenous), intramuscular, intranasal, sublingual, intratracheal, inhalation, ocular, vaginal, and rectal, e.g., using a suppository.

For oral administration, the compounds (i.e., inhibitors, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified or mixed with other components so that oral delivery of the derivative is efficacious. Generally, the chemical modification or mixture contemplated permits (a) longer half-lives; and (b) uptake into the blood stream from the stomach or intestine. Also desired is the increase in overall stability of the component or components and increase in circulation time in the body. Examples of such moieties or other compounds include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the inhibitor (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the inhibitor (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, $\alpha$-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as *acacia*, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the inhibitor or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

Exemplary Kits

The invention also includes kits. The kit has a container housing an inhibitor of the invention and optionally additional containers with other therapeutics such as anti-viral agents or viral vaccines. The kit also includes instructions for administering the component(s) to a subject who has or is at risk of having an enveloped viral infection.

In some aspects of the invention, the kit can include a pharmaceutical preparation vial, a pharmaceutical preparation diluent vial, and inhibitor. The vial containing the diluent for the pharmaceutical preparation is optional. The diluent vial contains a diluent such as physiological saline for diluting what could be a concentrated solution or lyophilized powder of inhibitor. The instructions can include instructions for mixing a particular amount of the diluent with a particular amount of the concentrated pharmaceutical preparation, whereby a final formulation for injection or infusion is prepared. The instructions may include instructions for use in an oral formulation, inhaler, intravenous injection or any other device useful according to the invention. The instructions can include instructions for treating a patient with an effective amount of inhibitor. It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

We claim:

1. A compound represented by formula II:

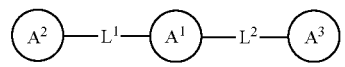

or a pharmaceutically acceptable salt, solvate, hydrate, chemically-protected form, enantiomer or stereoisomer thereof; wherein, independently for each occurrence,

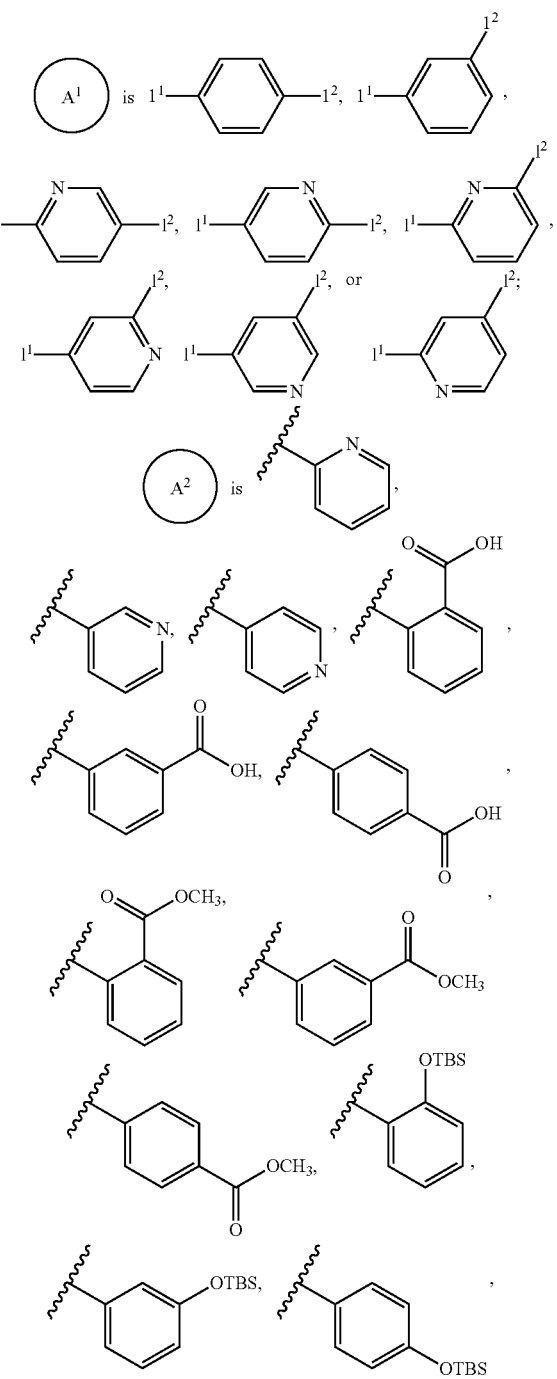

-continued

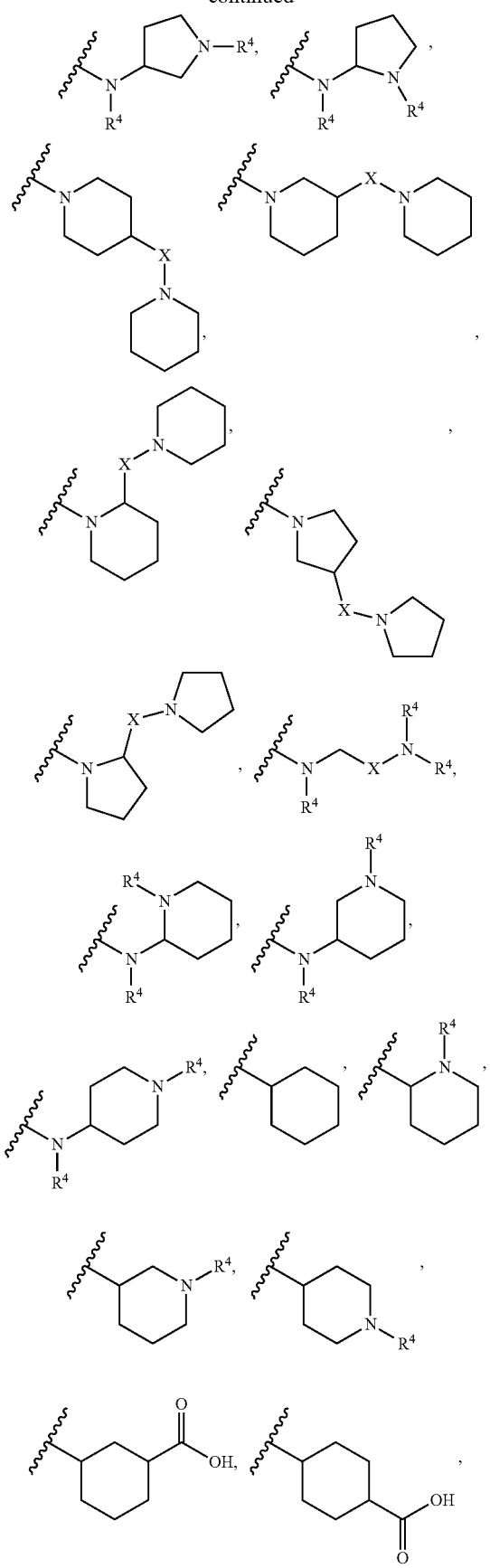
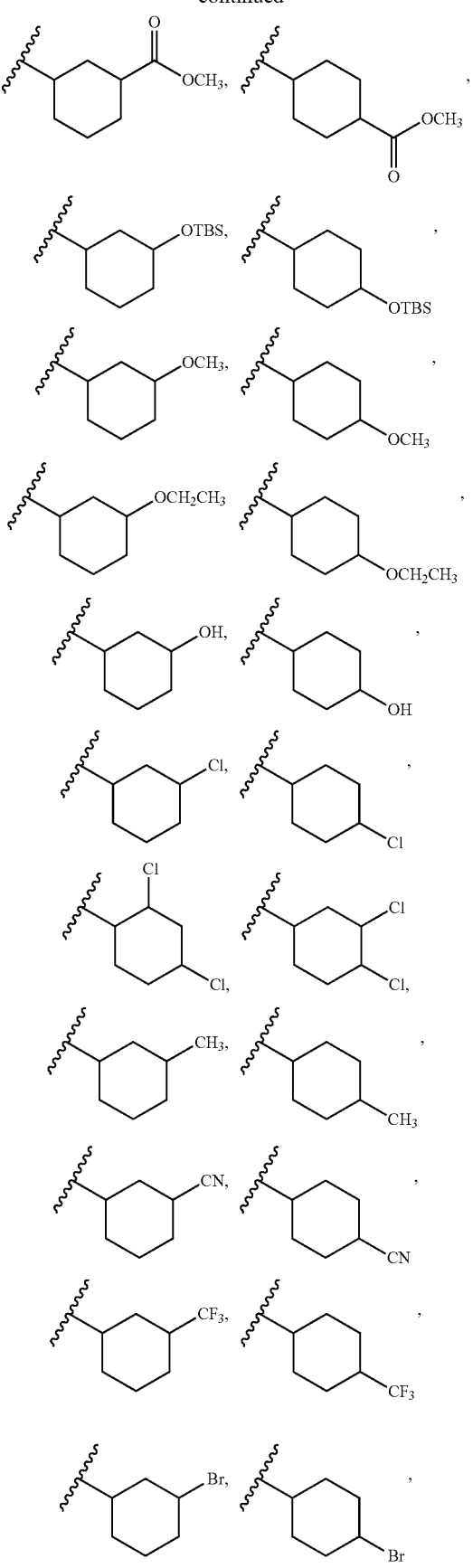

-continued

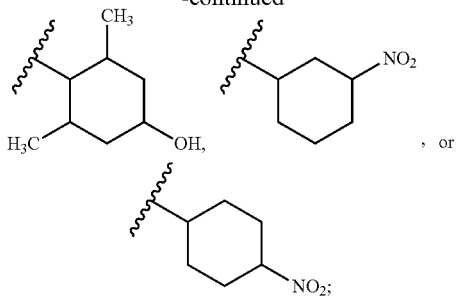, or

L¹ is

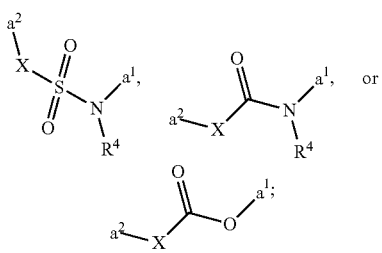

L² is

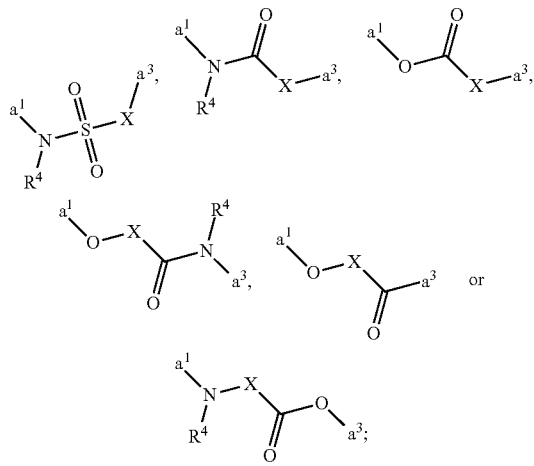

l¹ is a bond to L¹;
l² is a bond to L²;
a¹ is a bond to

Ⓐ¹ ;

a² is a bond to

Ⓐ² ;

a³ is a bond to

Ⓐ³ ;

X is a bond,

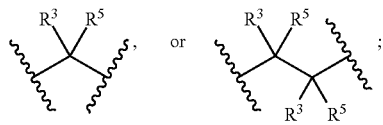

$R^3$ is hydrogen or alkyl;
$R^4$ is hydrogen, alkyl, aralkyl, or alkylcarbonyl; and
$R^5$ is hydrogen, or alkyl, haloalkyl, or alkyl substituted with hydroxy, cyano, carboxy, aralkyloxy, alkyloxycarbonyl or aralkyloxycarbonyl;

provided that the compound is not

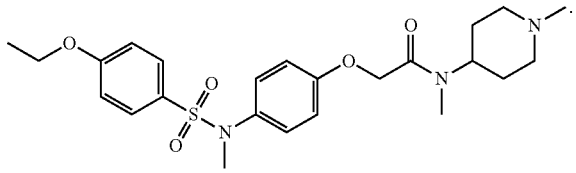 [SMILES: CCOc1ccc(S(=O)(=O)N(C)c2ccc(OCC(=O)N(C)C3CCN(C)CC3)cc2)cc1]

2. The compound of claim 1, wherein

Ⓐ¹ is l¹—⟨phenyl⟩—l².

3. The compound of claim 1, wherein

Ⓐ² is 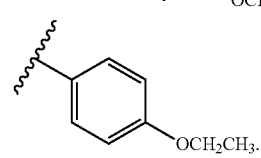

4. The compound of claim 1, wherein

Ⓐ² is ⟨phenyl⟩—OCH₃.

5. The compound of claim 1, wherein
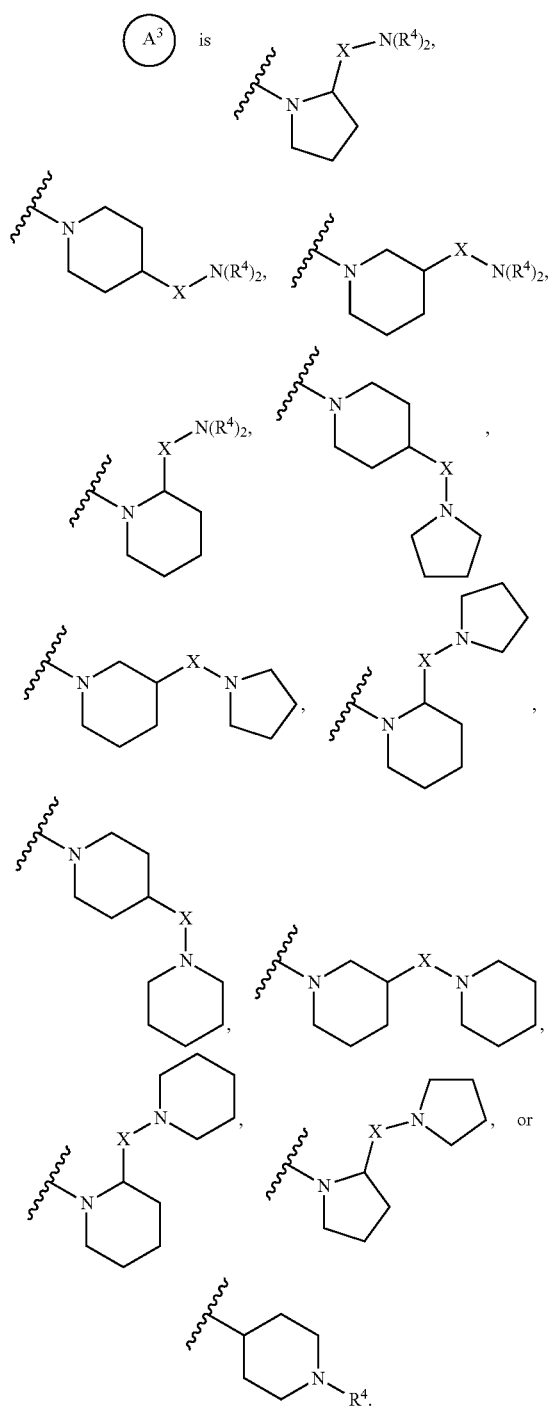
6. The compound of claim 1, wherein
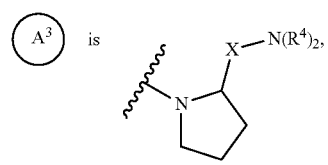
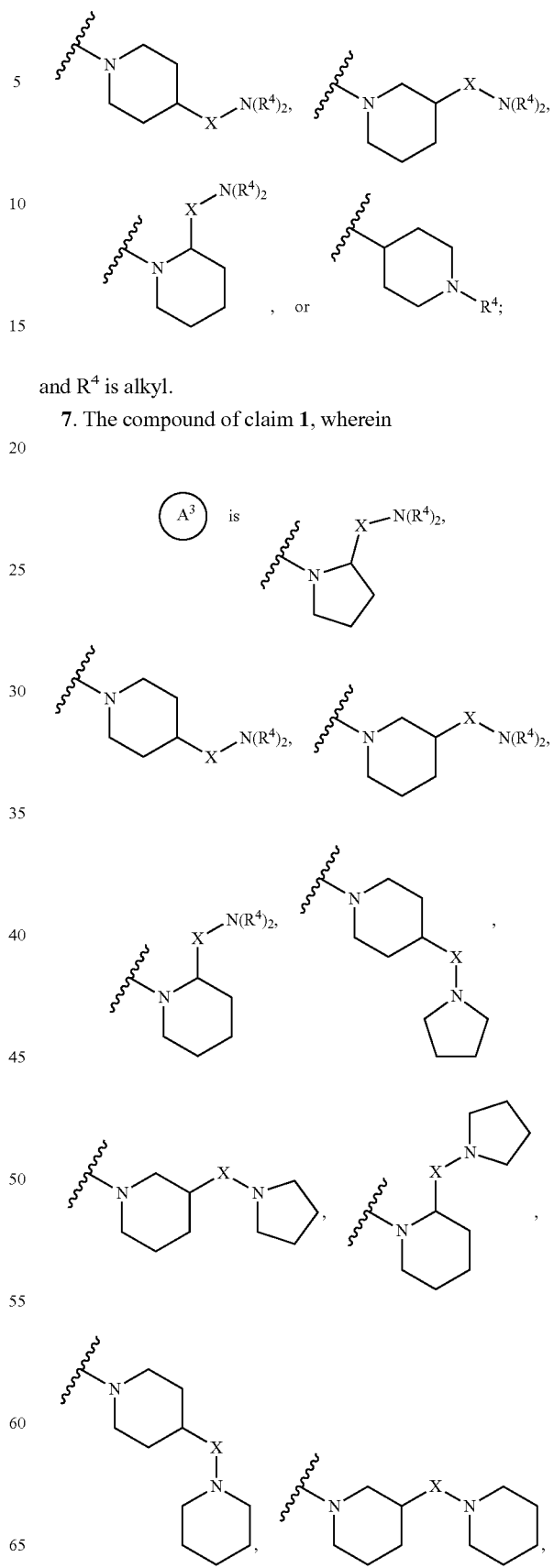
and $R^4$ is alkyl.
7. The compound of claim 1, wherein -continued
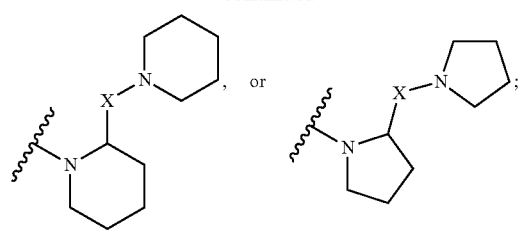
and X is
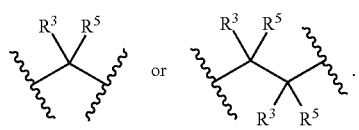
8. The compound of claim 1, wherein
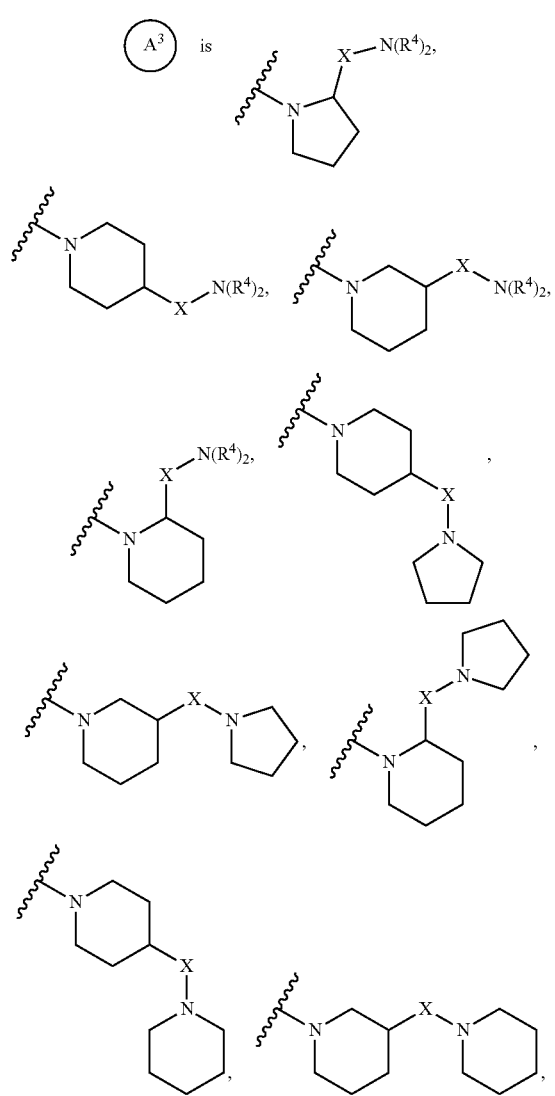
-continued
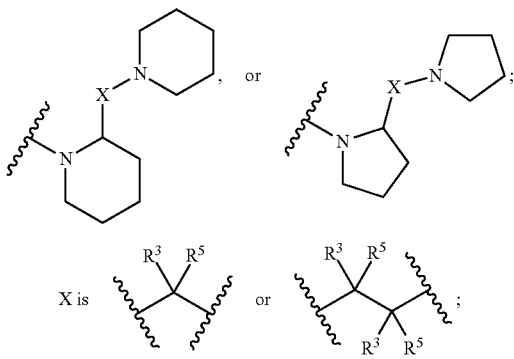
X is
and $R^3$ and $R^5$ are hydrogen.
9. The compound of claim 1, wherein
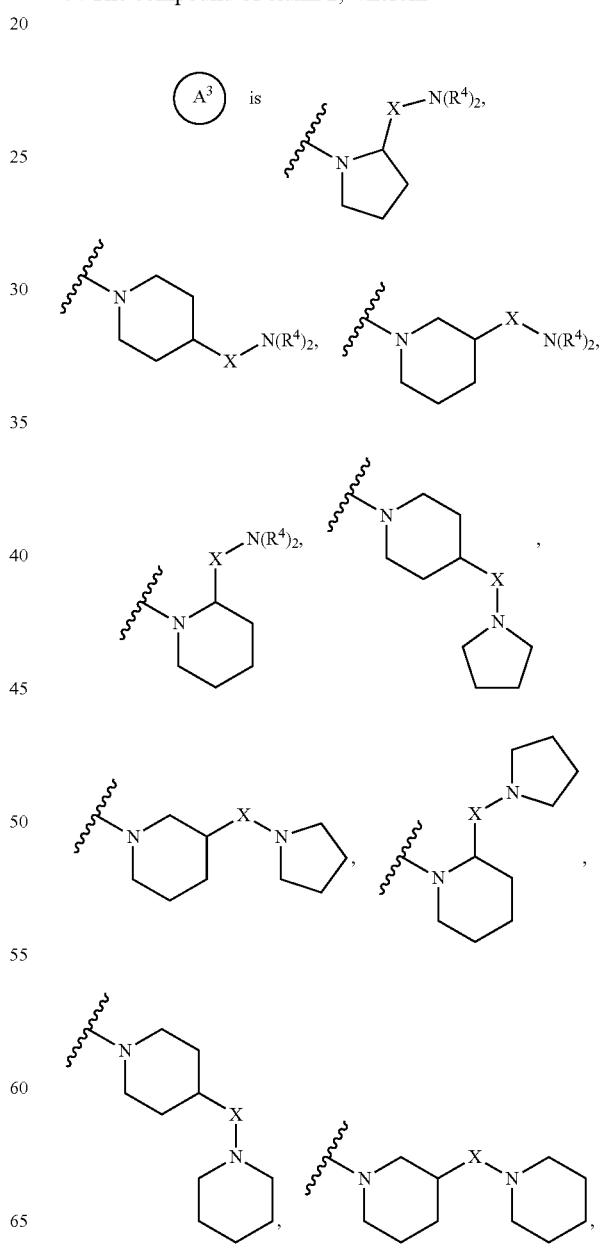

-continued
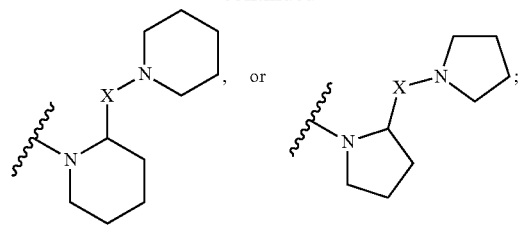
and X is a bond.
10. The compound of claim 1, wherein
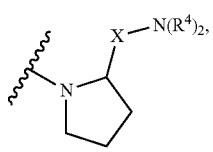 is
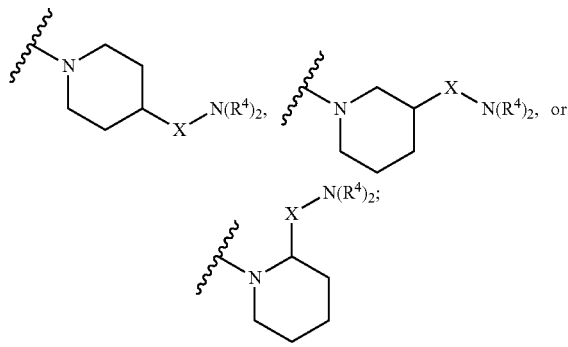
X is a bond; and $R^4$ is alkyl.
11. The compound of claim 1, wherein $L^1$ is
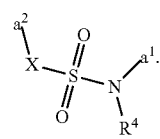
12. The compound of claim 1, wherein $L^1$ is
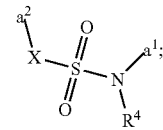
and X is a bond.
13. The compound of claim 1, wherein $L^2$ is
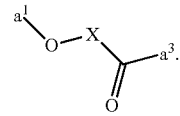
14. The compound of claim 1, wherein $L^2$ is
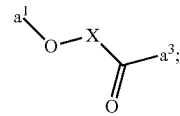
and X is —CH$_2$—.
* * * * *